United States Patent [19]

Sato et al.

[11] Patent Number: 5,637,253
[45] Date of Patent: Jun. 10, 1997

[54] CHIRAL SMECTIC LIQUID CRYSTAL COMPOUND, CHAIN POLYMERIC LIQUID CRYSTAL COPOLYMER COMPOUND, THEIR POLYMERIC LIQUID CRYSTAL COMPOSITION, A POLYMERIC LIQUID CRYSTAL DEVICE WHICH USES THEM, AND APPARATUS AND METHOD WHICH USES THE SAME

[75] Inventors: Koichi Sato, Yamato; Kazuo Yoshinaga, Machida; Yomishi Toshida, Yokohama; Takeo Eguchi, Atsugi, all of Japan

[73] Assignee: Canon Kabushiki Kaisha, Tokyo, Japan

[21] Appl. No.: 400,485

[22] Filed: Mar. 8, 1995

Related U.S. Application Data

[63] Continuation of Ser. No. 868,344, Apr. 15, 1992, abandoned.

[30] Foreign Application Priority Data

Apr. 18, 1991 [JP] Japan ..................... 3-112157
Apr. 8, 1992 [JP] Japan ..................... 4-114265

[51] Int. Cl.$^6$ .......................... C09K 19/52; C09K 19/34
[52] U.S. Cl. ......................... 252/299.01; 252/299.6
[58] Field of Search ..................... 252/299.01, 299.6

[56] References Cited

U.S. PATENT DOCUMENTS 4,367,924  1/1983  Clark et al. ..................... 350/334
4,798,680  1/1989  Nohira et al. ..................... 252/299.01

(List continued on next page.)

FOREIGN PATENT DOCUMENTS 0338845  10/1989  European Pat. Off. .
0361843   4/1990  European Pat. Off. .

(List continued on next page.)

OTHER PUBLICATIONS

World Patents Index Latest, Week 9134, An 91–249433. 1991.
Patent Abstracts of Japan, vol. 14, No. 456 (Oct. 1990). C–765 (2).
Schadt et al., Applied Physics Letters, vol. 18, No. 4 (1971) 127:8.

(List continued on next page.)

*Primary Examiner*—Cynthia Harris Kelly
*Attorney, Agent, or Firm*—Fitzpatrick, Cella, Harper & Scinto

[57] ABSTRACT

A chain polymeric liquid crystal compound having a structure expressed by the following general formula [I] as a flexible spacer and a chain polymeric liquid crystal copolymer compound, a polymeric liquid crystal composition containing at least one of their compounds and at least any one of a polymeric compound, a polymeric liquid crystal compound, a low molecular weight liquid crystal compound and a low molecular weight liquid crystal compound, a polymeric liquid crystal device which uses the same, and an apparatus and a method which use the polymeric liquid crystal device:

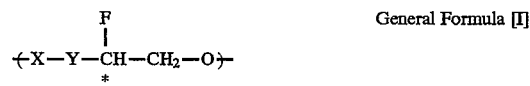

General Formula [I]

(where X is —O—, —O—CH$_2$—CH$_2$—, —O—CH$_2$—,

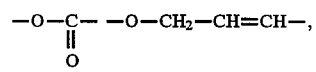

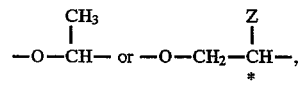

Y is —(CH$_2$)$_n$— (n=1 to 18), Z is a halogen atom, an alkyl group or an alkoxy group, and * is an asymmetric carbon atom).

30 Claims, 4 Drawing Sheets

U.S. PATENT DOCUMENTS

| | | | |
|---|---|---|---|
| 4,820,026 | 4/1989 | Okada et al. | 350/341 |
| 4,844,835 | 7/1989 | Uchida et al. | 252/299.01 |
| 4,892,675 | 1/1990 | Nohira et al. | 252/299.01 |
| 4,913,839 | 4/1990 | Uchida et al. | 252/299.01 |
| 5,171,470 | 12/1992 | Nohira et al. | 252/299.01 |
| 5,185,097 | 2/1993 | Toshida et al. | 252/299.01 |
| 5,288,426 | 2/1994 | Itoh et al. | 252/299.5 |

FOREIGN PATENT DOCUMENTS

| | | |
|---|---|---|
| 0376344 | 7/1990 | European Pat. Off. . |
| 107216 | 8/1981 | Japan . |
| 072784 | 4/1988 | Japan . |
| 099204 | 4/1988 | Japan . |
| 161005 | 7/1988 | Japan . |

OTHER PUBLICATIONS

Shibaev et al., Polymer Communications, vol. 24, No. 12 (1983) 364:5.

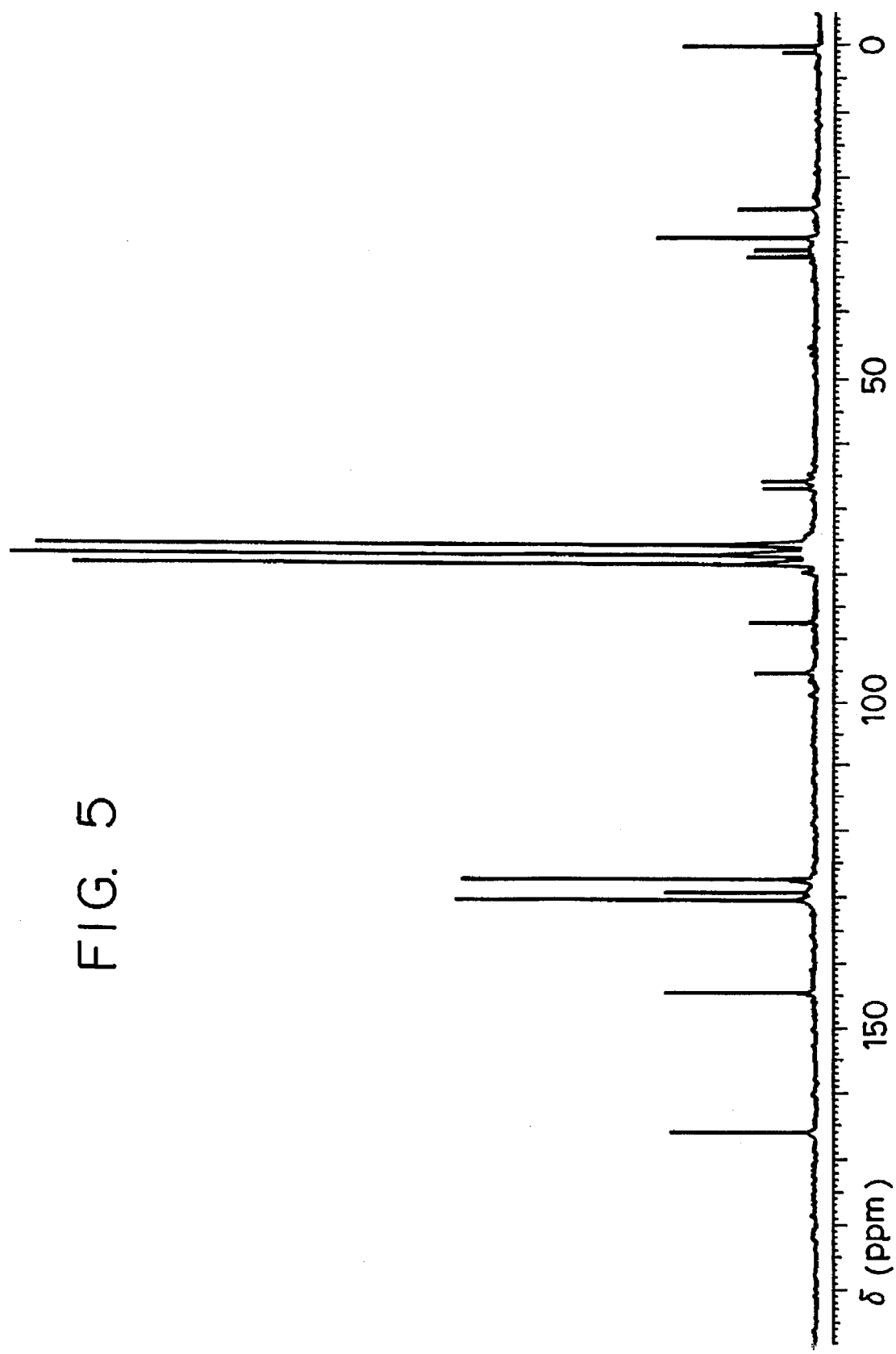

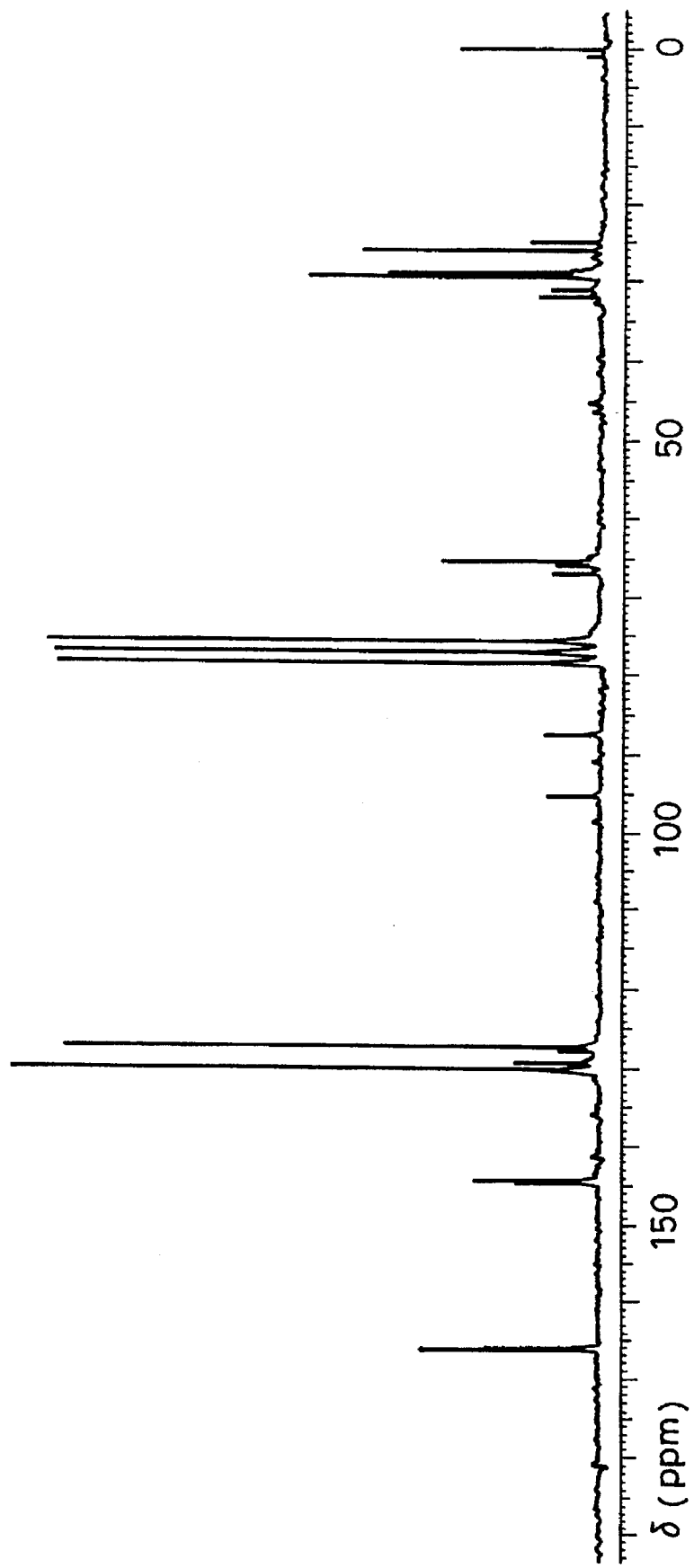

CHIRAL SMECTIC LIQUID CRYSTAL COMPOUND, CHAIN POLYMERIC LIQUID CRYSTAL COPOLYMER COMPOUND, THEIR POLYMERIC LIQUID CRYSTAL COMPOSITION, A POLYMERIC LIQUID CRYSTAL DEVICE WHICH USES THEM, AND APPARATUS AND METHOD WHICH USES THE SAME

This application is a continuation of application Ser. No. 07/868,344, filed Apr. 15, 1992, now abandoned.

BACKGROUND OF THE INVENTION

1. Field of the Invention

The present invention relates to a novel chain polymeric liquid crystal compound, a chain polymeric liquid crystal copolymer compound, each of which has a fluoro group in a flexible spacer portion thereof, their chain polymeric liquid crystal compound, a polymeric liquid crystal composition containing the chain polymeric liquid crystal copolymer compound, their chain polymeric liquid crystal compound, a polymeric liquid crystal device which uses the chain polymeric liquid crystal copolymer compound or the polymeric liquid crystal composition, and an apparatus and a method which use the same.

The chain polymeric liquid crystal compound, the chain polymeric liquid crystal copolymer compound and the polymeric liquid crystal composition according to the present invention can be used as optoelectronic material and optical equipment material and the like represented by a display and a memory.

2. Description of the Prior Art

There has been known a conventional liquid crystal device which uses twisted nematic liquid crystals disclosed in "Voltage Dependent Optical Activity of a Twisted Nematic Liquid Crystal" written by M. Schadt and W. Helfrich, pp. 127 to 128, No. 4, Vol. 18 of *Applied Physics Letters* (Feb. 15, 1971). However, the aforesaid TN liquid crystal encounters a problem in that crosstalk is generated during a time-division operation in which a matrix electrode structure, in which the pixel density is high, is employed. Therefore, a limit exists on the number of the pixels.

What is even worse, the electric field response is unsatisfactory and the characteristic of angle of visibility is insufficient. Therefore, the use of TN liquid crystals as a display has been limited. Furthermore, since a manufacturing process for forming a thin film transistor in each pixel is too complicated, it is very difficult to manufacture a display device having a large area.

In order to overcome the aforesaid problems experienced with the conventional liquid crystal device, use of a liquid crystal device having bistability has been suggested by Clark and Lagerwall (refer to Japanese Patent Laid-Open No. 56-107216 and the specification of U.S. Pat. No. 4,367,924 and the like).

As the bistable liquid crystal, a ferroelectric liquid crystal composed of chiral smectic phase-C (Sm*C) or phase-H (Sm*H) has been usually employed. The ferroelectric liquid crystal enables a very high response speed to be realized, and as well, bistability having a memory characteristic can be realized because of its spontaneous polarization. Furthermore, an excellent visible angle characteristic can be realized. Therefore, it is considered to be a preferable material for a display having large capacity and large area. However, there arises a technical problem in a case where a liquid crystal cell is formed in that a large area display device cannot easily be manufactured because it is difficult to make a large area which will be monodomain.

A structure has been known in which a polymeric liquid crystal is used as a memory medium.

For example, a heat writing memory is known which has been disclosed in "Thermotropic Liquid Crystalline Polymers. 14", pp. 364 to 365, Vol. 24 of *Polymer Communications* written by V. Shibaev, S. Kostromin, N. Pla'te, S. Ivaov, V. Vestrov, and I. Yakovlev.

However, the polymeric liquid crystal compound suffers from its insufficiently high glass transition point realized in a case where the memory medium having the polymeric liquid crystal is used to store recorded data by utilizing its glass transition point. Another problem arises in that the response speed is unsatisfactorily lowered due to the polymerizing process. Therefore, it has not been put to practical use.

Furthermore, a side chain type ferroelectric polymeric liquid crystal has been disclosed in Japanese Patent Laid-Open No. 63-72784 (see counterpart U.S. Pat. Nos. 4,844,835 and 4,913,839), Japanese Patent Laid-Open No. 63-99204 (same U.S. counterparts) and Japanese Patent Laid-Open No. 63-161005. However, the side chain type polymeric liquid crystal encounters a problem in that a uniform orientation cannot easily be realized by the stretching orientation which is the simplest orientation means.

On the other hand, a chain ferroelectric polymeric liquid crystal having a hydrocarbon type chiral diol has been reported in *polymer Preprints, Japan*, Vol. 38, No. 8, p.p. 2371 to 2373 (1989) by a group including Watanabe. However, a satisfactorily large spontaneous polarization cannot be obtained and thereby the realized response speed is too low because a hydrocarbon chiral diol is used as the chiral group.

SUMMARY OF THE INVENTION

In order to overcome the aforesaid problems experienced with the conventional technology, an object of the present invention is to provide a novel chain polymeric liquid crystal compound, a chain polymeric liquid crystal copolymer compound, each of which has a fluoro group in a flexible spacer portion thereof, with which a large area device can be formed as an optoelectronic material and optical equipment material and the like, a satisfactorily large spontaneous polarization and excellent response characteristics can be obtained, a polymeric liquid crystal composition which contains any one of the aforesaid compounds, a polymeric liquid crystal device which uses the compound or the polymeric liquid crystal composition, and an apparatus and a method which respectively use the same.

After a study made in order to overcome the problems experienced with the aforesaid conventional technology, the inventors found a novel chain polymeric liquid crystal compound, a chain polymeric liquid crystal copolymer compound, each of which has a fluoro group in a flexible spacer portion thereof, and a polymeric liquid crystal composition which contains either of the aforesaid compounds. Furthermore, they found that the aforesaid chain polymeric liquid crystal compound, the chain polymeric liquid crystal copolymer compound and a polymeric liquid crystal composition has an excellent response characteristic and a large area liquid crystal device can be formed by utilizing the characteristics of the polymer, so that an excellent polymeric liquid crystal device, an apparatus and a method of its use can be provided.

According to a first aspect of the invention, there is provided a chain polymeric liquid crystal compound having a structure expressed by the following general formula [I] as a flexible spacer:

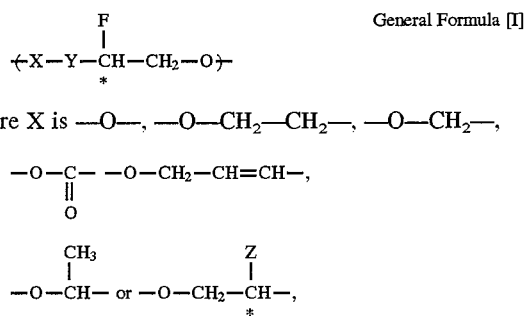

General Formula [I]

(where X is —O—, —O—CH$_2$—CH$_2$—, —O—CH$_2$—,

—O—C— —O—CH$_2$—CH=CH—,
‖
O

—O—CH— or —O—CH$_2$—CH—,
 |                  |
 CH$_3$              Z
                    *

Y is —(CH$_2$)$_n$— (n=1 to 18), Z is a halogen atom, an alkyl group or an alkoxy group, and * is an asymmetric carbon atom).

According to a second aspect of the invention, there is provided a polymeric liquid crystal composition which contains at least one of the chain polymeric liquid crystal compound having the structure expressed by general formula [I] as the flexible spacer according to the first aspect of the invention and at least any one of a polymeric compound, a polymeric liquid crystal compound, a low molecular compound and a low molecular liquid crystal compound.

According to a third aspect of the invention, there is provided a polymeric liquid crystal device which uses a polymeric liquid crystal composition having the structure expressed by general formula [I] as the flexible spacer according to the first aspect of the invention or at least one of the chain polymeric liquid crystal compound and at least any one of a polymeric compound, a polymeric liquid crystal compound, a low molecular compound and a low molecular liquid crystal compound.

According to a fourth aspect of the invention, there is provided an apparatus which uses the polymeric liquid crystal device according to the third aspect of the invention.

According to a fifth aspect of the invention, there is provided a method of using the chain polymeric liquid crystal compound and the polymeric liquid crystal composition respectively according to the first and the second aspects of the invention.

According to a sixth aspect of the invention, there is provided a chain polymeric liquid crystal copolymer compound having the structure expressed by general formula [I] as the flexible spacer.

According to a seventh aspect of the invention, there is provided a polymeric liquid crystal composition which contains at least one of the chain polymeric liquid crystal copolymer compound having the structure expressed by general formula [I] as the flexible spacer according to the sixth aspect of the invention and at least one of a polymeric compound, a polymeric liquid crystal compound, a low molecular compound and a low molecular liquid crystal compound.

According to an eighth aspect of the invention, there is provided a polymeric liquid crystal device which uses a polymeric liquid crystal composition which contains at least one of the chain polymeric liquid crystal copolymer compound having the structure expressed by general formula [I] as the flexible spacer according to the seventh aspect of the invention or at least one of the chain polymeric liquid crystal compound and at least any one of a polymeric compound, a polymeric liquid crystal compound, a low molecular compound and a low molecular liquid crystal compound.

According to a ninth aspect of the invention, there is provided an apparatus which uses the polymeric liquid crystal device according to the eighth aspect of the invention.

According to a tenth aspect of the invention, there is provided a method of using the chain polymeric liquid crystal copolymer compound or the polymeric liquid crystal composition respective according to the sixth and seventh aspects of the inventions.

BRIEF DESCRIPTION OF THE DRAWINGS

FIG. 5 illustrates $^{13}$C-NMR (included in CDCl$_3$) of polymer a; and

FIG. 6 illustrates $^{13}$C-NMR (included in CDCl$_3$) of polymer e.

DETAILED DESCRIPTION OF THE PREFERRED EMBODIMENTS

Figure 1:
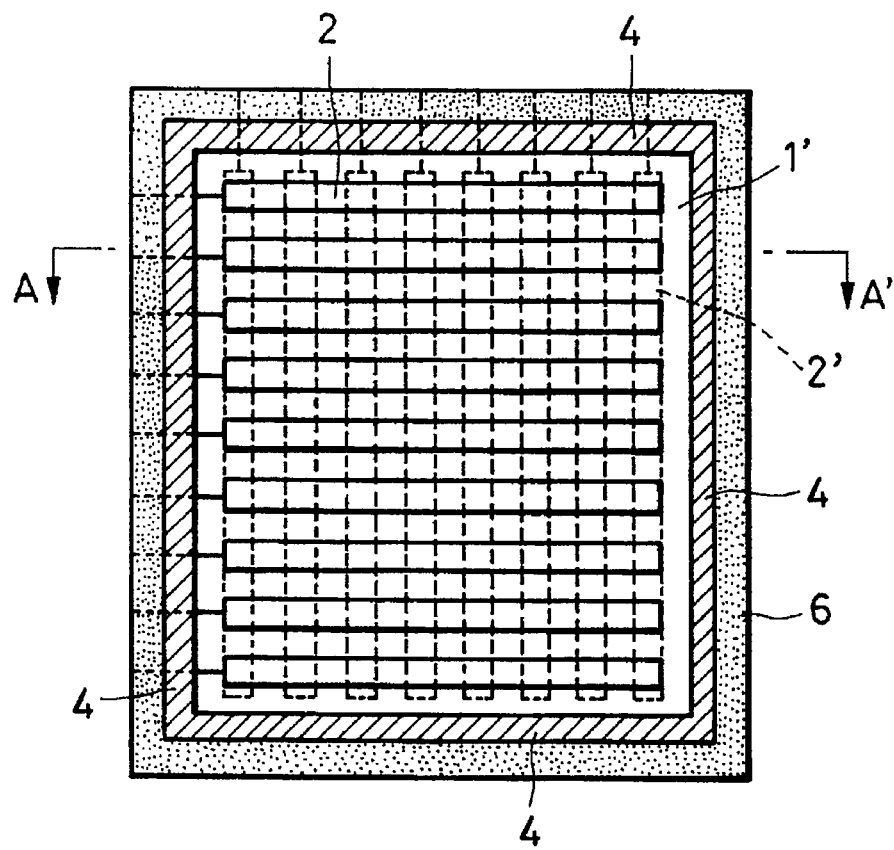
FIG. 1 is a plan view which illustrates an example of a polymeric liquid crystal device according to the present invention.

A chain polymeric liquid crystal compound according to a first invention of the present invention has a structure expressed by the following general formula [I] as a flexible spacer thereof:

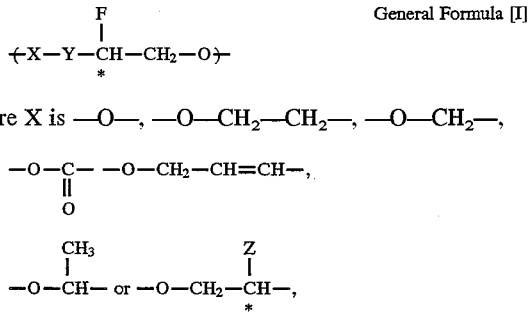

General Formula [I]

(where X is —O—, —O—CH$_2$—CH$_2$—, —O—CH$_2$—,

—O—C— —O—CH$_2$—CH=CH—,
‖
O

—O—CH— or —O—CH$_2$—CH—,
 |                  |
 CH$_3$              Z
                    *

Y is —(CH$_2$)$_n$— (n=1 to 18), Z is a halogen atom, an alkyl group or an alkoxy group, and * is an asymmetric carbon atom).

The chain polymeric liquid crystal compound according to the present invention has the aforesaid flexible spacer portion expressed by General Formula [I] and has a mesogen portion formed by a substitutable aromatic circle or an aliphatic circle. Specifically, it is exemplified by:

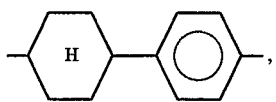

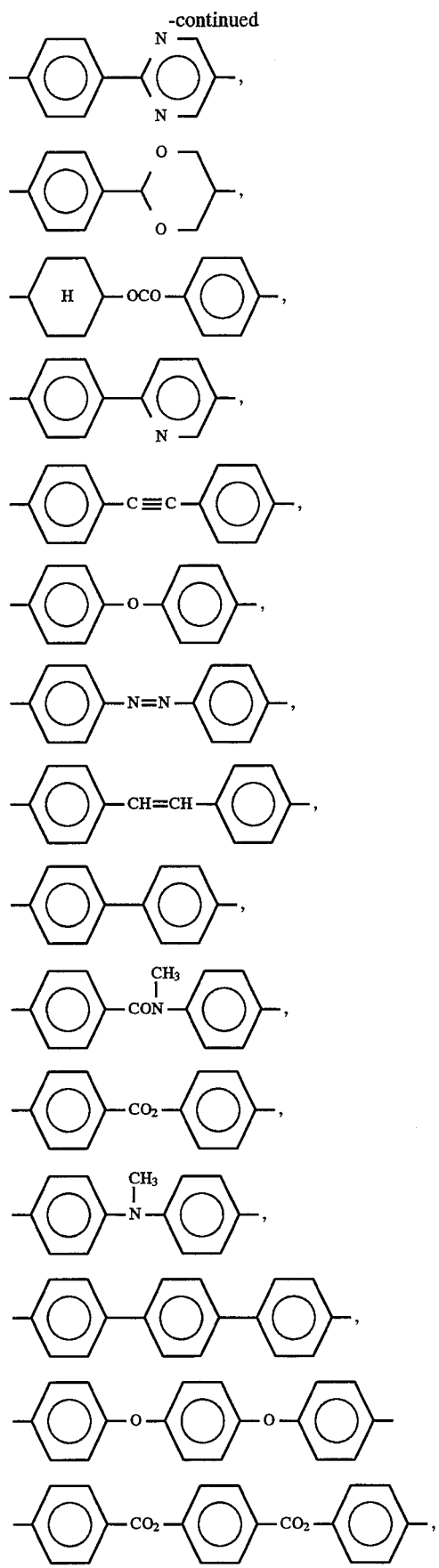
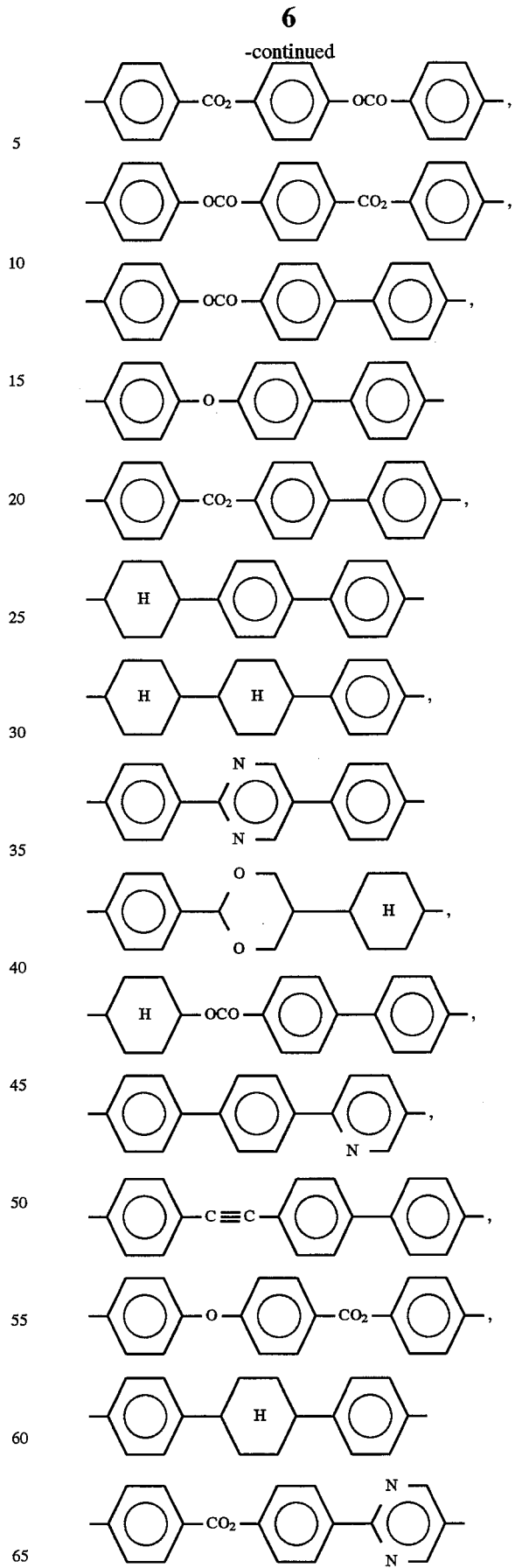

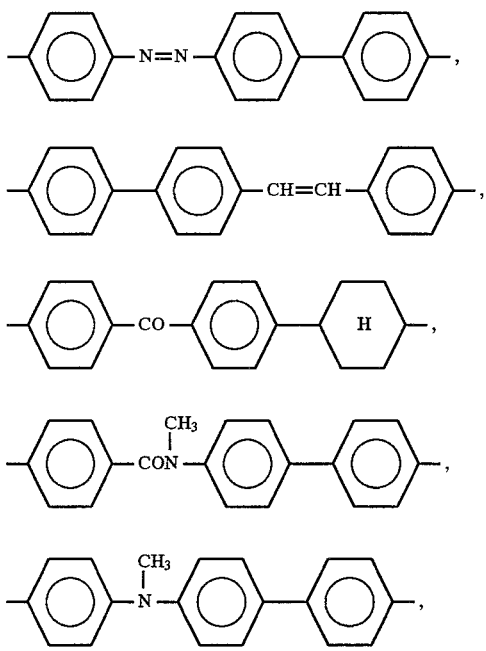

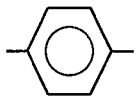

It is preferable that the mesogen portion is formed by only ring according to the present invention.

The chain polymeric liquid crystal compound has the aforesaid flexible spacer portion and the mesogen portion each of which is bonded by a selected bonding base (such as an ether, ester or a carbonate bond).

It is preferable that the aforesaid chain polymeric liquid crystal compound is the polyester compound because the liquid crystal characteristics can easily be displayed.

The chain polymeric liquid crystal compound according to the present invention may be exemplified by the following structure (bonding base included), where n=1 to 18:

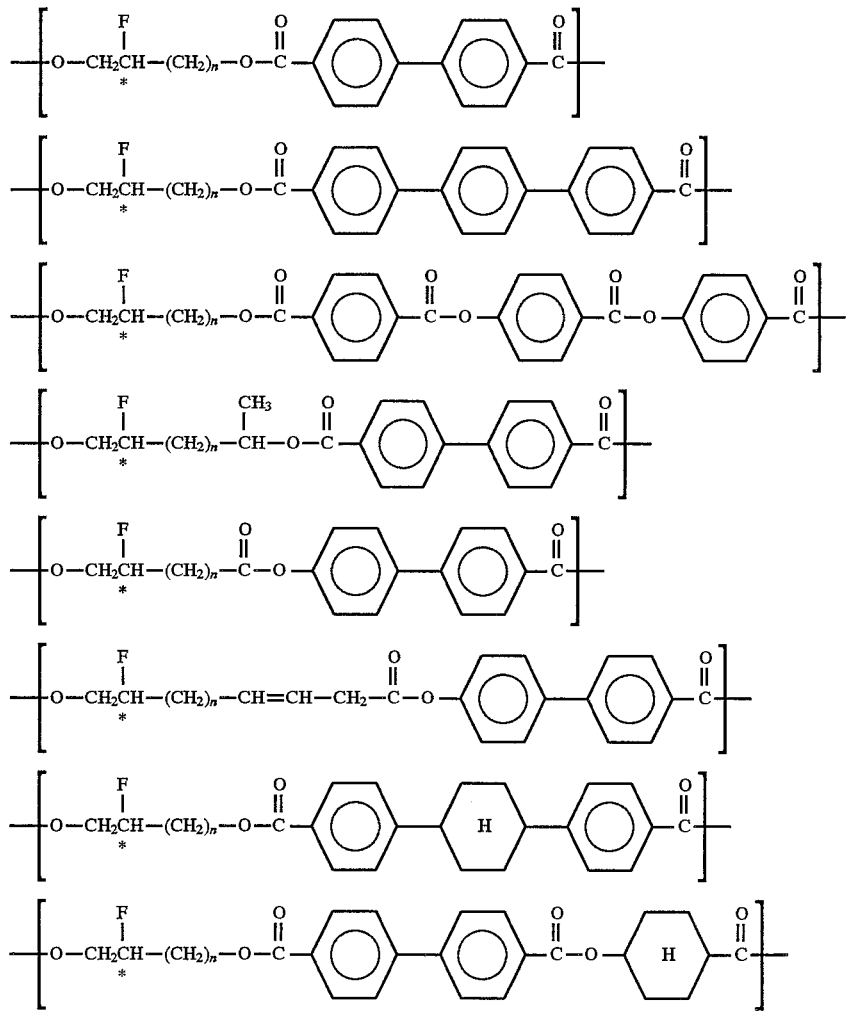

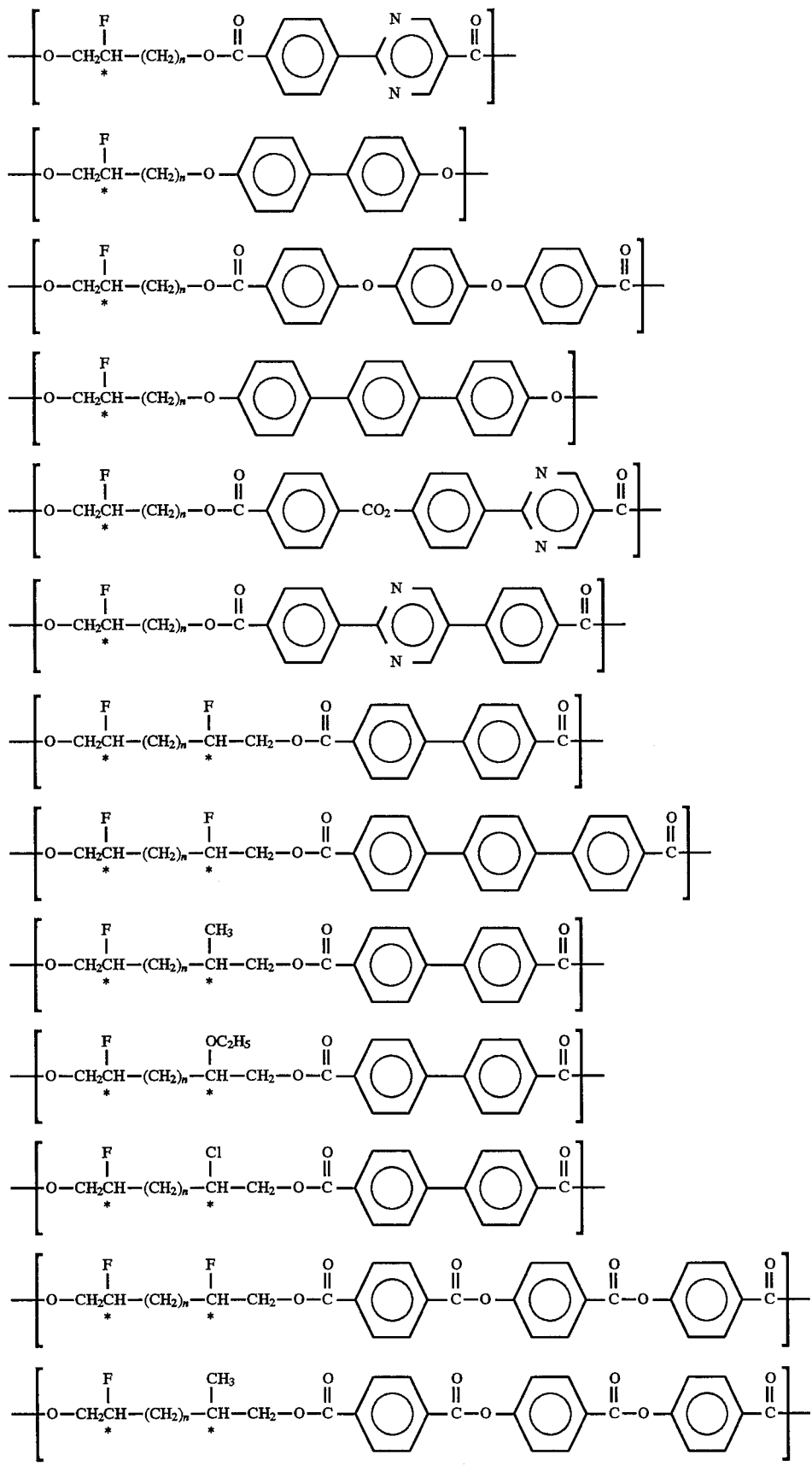

-continued

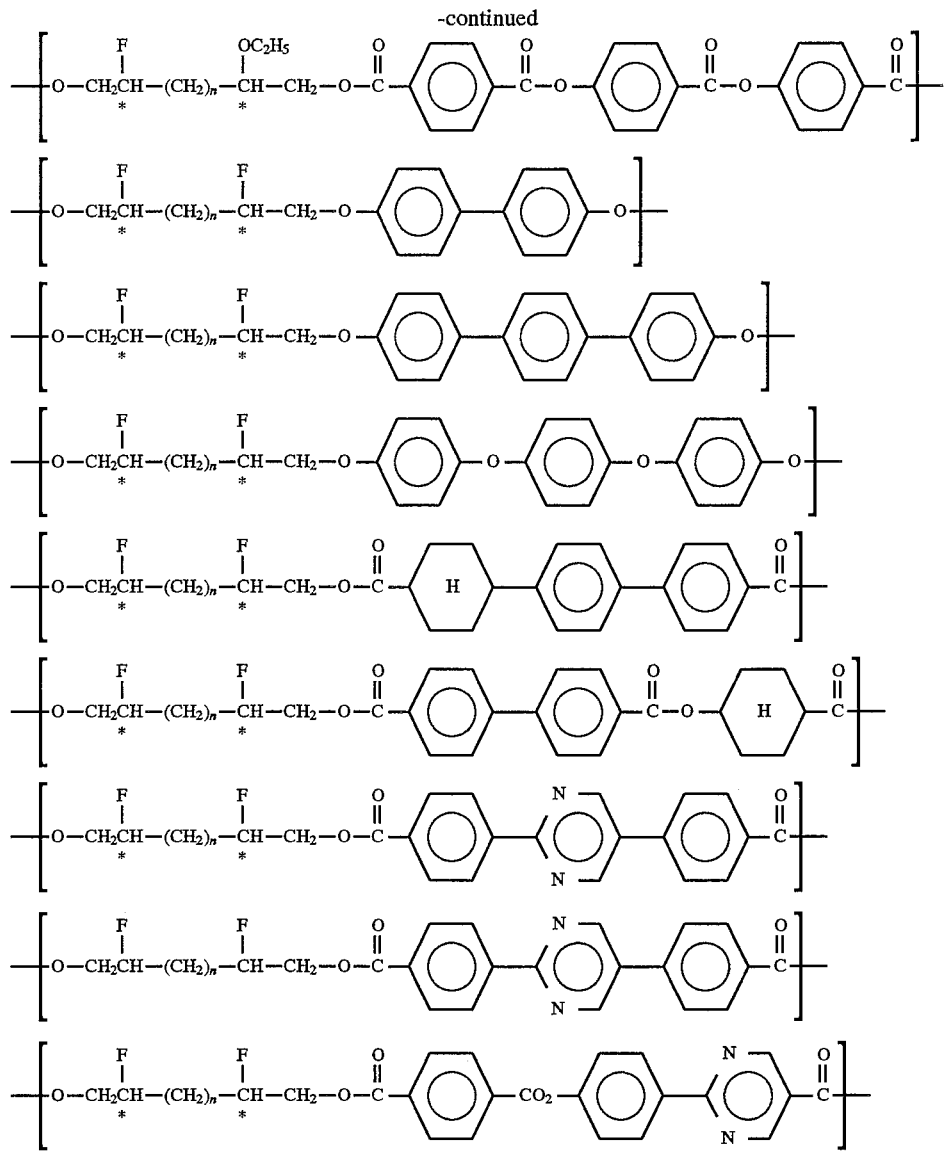

The numerical average molar weight of the chain polymeric liquid crystal compound according to the present invention is 2,000 to 1,000,000, preferably 2,000 to 500,000. If it is less than 2,000, the film forming characteristic of the polymeric liquid crystal compound deteriorates, causing a problem to arise in its formability as a film formed by a coating process. If it is larger than 1,000,000, the responsiveness to the external field is deteriorated with the rise in the viscosity.

As a sole compound or a composition, the chain polymeric liquid crystal compound according to the present invention has the fluorine base having a large bipolar moment in the chiral portion thereof in a case where the chiral smectic phase having ferroelectricity is shown. Therefore, it exhibits an advantage of a very high response speed because of its large spontaneous polarization as compared with the conventional hydrocarbon type chiral group and the halogen type chiral group. Furthermore, its large intermolecular force can be enlarged due to the polarity possessed by fluorine, so that advantages can be obtained in that the liquid crystal characteristics can be displayed in a wide range and that the smectic liquid crystal phase can easily be realized.

Furthermore, the carbon-fluorine bond exhibits very significant bonding energy and thereby displays extreme stability, so that it is stable physically and chemically as compared with the halogen type chiral group.

In addition, in a structure which contains the chain polymeric liquid crystal compound according to the present invention, uniform orientation, which has been very difficult to perform in the low molecular ferroelectric liquid crystal and the ferroelectric side chain type polymeric liquid crystal, can easily be performed by a stretching method or a fusion extruding method, or the like.

A method of manufacturing the chain polymeric liquid crystal compound according to the present invention will now be described. Although it can be manufactured by a conventional method which uses polyester, or polyether, or the like, polymerization cannot proceed smoothly in a case of the polyester compound because a decomposing reaction takes place in the halogen portion due to the high temperature required in the melting polymerization method. Accordingly, the following method for manufacturing the polyester compound according to the present invention is preferably employed.

That is, a diol having dicarboxylic acid dichloride and a fluorine group is subjected to a dehydro-chlorination reaction in a solution, so that the chain polymeric liquid crystal polyester compound is manufactured. The dicarboxylic dichloride is exemplified by the following compounds:
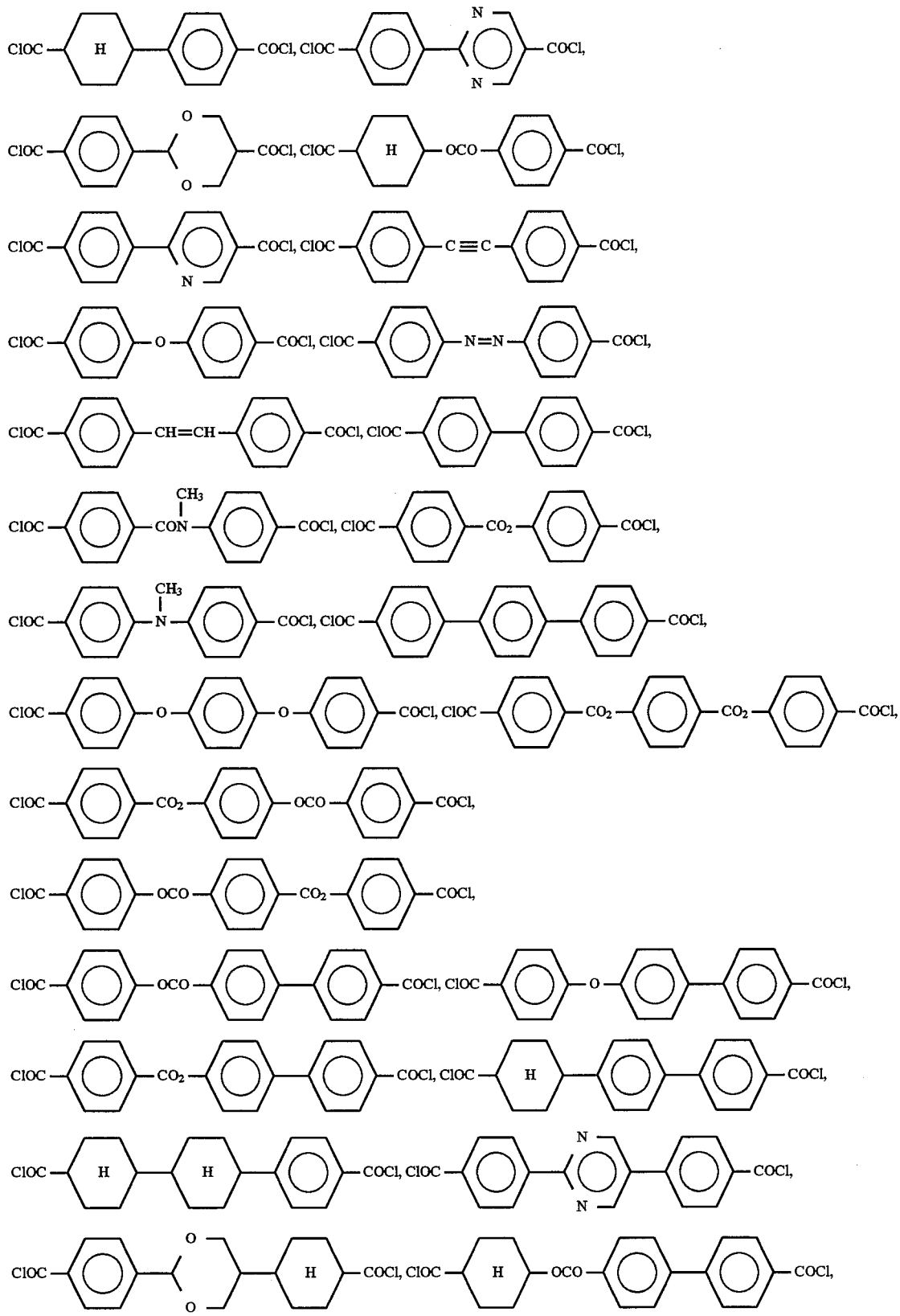

-continued

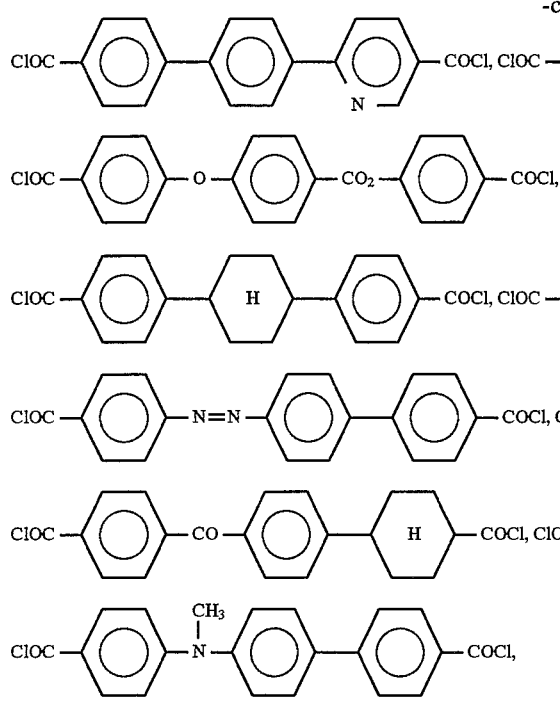

The diol is exemplified by the following compounds:

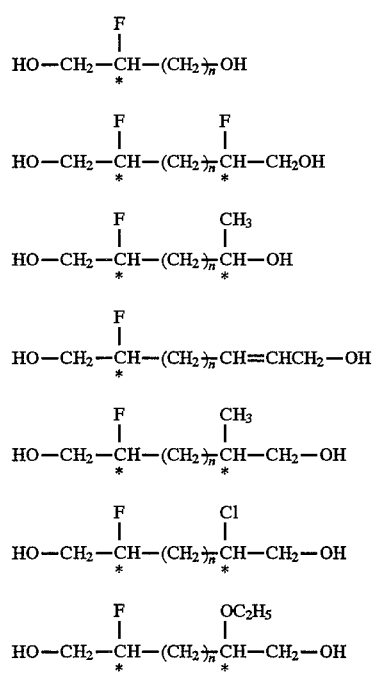

The solvent for use in the reaction must be an aprotic solvent exemplified by chloroform, benzene, toluene, DMF, DMSO, HMPA, tetrachloroethane, THF, diphenylether, and ethylene glycol dimethyl ether and the like. In order to prevent the hydrolysis of the dicarboxyliyc acid dichloride by water contained in the solvent, water must be reduced from the solvent as much as possible. For the same reason, it is preferable that the reaction be carried out under an atmosphere of $N_2$, Ar, or He or the like in place of air.

In order to catch hydrogen chloride, amine such as pyridine may be added to the system.

The reaction temperature must be 300° C. or lower which is lower than the boiling point of the employed solvent and to control the decomposition of the diol having the fluorine group, preferably 250° C. or lower, still more preferably 200° C. or lower.

In order to allow the polymerizing reaction to proceed smoothly, it is preferable that the temperature be 50° C. or higher, preferably 100° C. or higher.

With the aforesaid manufacturing method, the density of the reactive base can be lowered because the reaction is performed at a low temperature and as well, the solvent reaction is employed, so that the decomposition of the diol having the fluorine group is controlled and the polymerizing reaction is allowed to smoothly proceed. As a result, polymers can easily be generated.

According to the second aspect of the invention, there is provided a polymeric liquid crystal composition which contains at least one of the chain polymeric liquid crystal compound having the chain polymeric liquid crystal compound according to the first aspect of the invention and at least any one of a polymeric compound, a polymeric liquid crystal compound, a low molecular compound and a low molecular liquid crystal compound. It is preferable that a compound to be blended with the chain polymeric liquid crystal compound according to the first invention be polymeric liquid crystal or low molecular liquid crystal.

The polymeric liquid crystal is exemplified by:

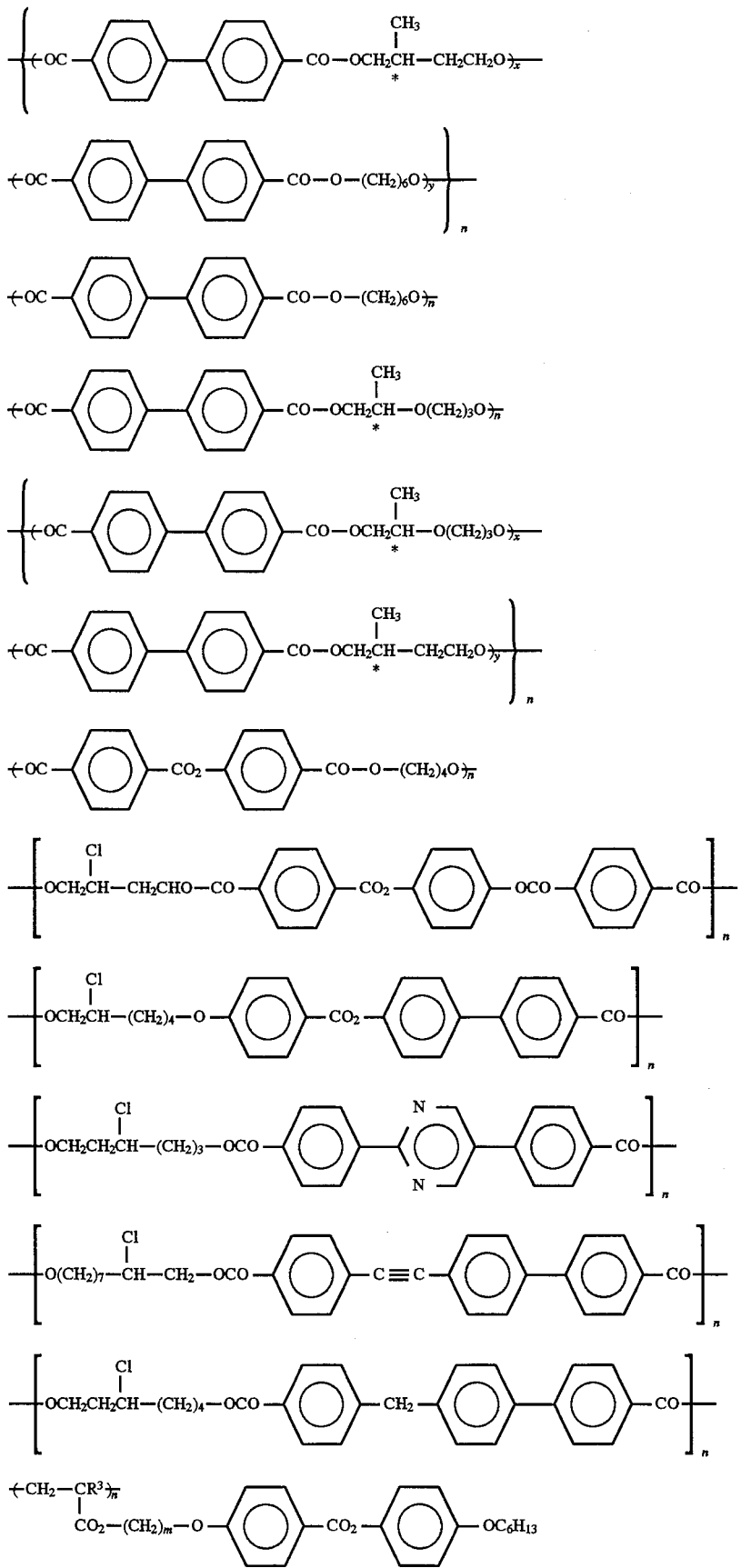

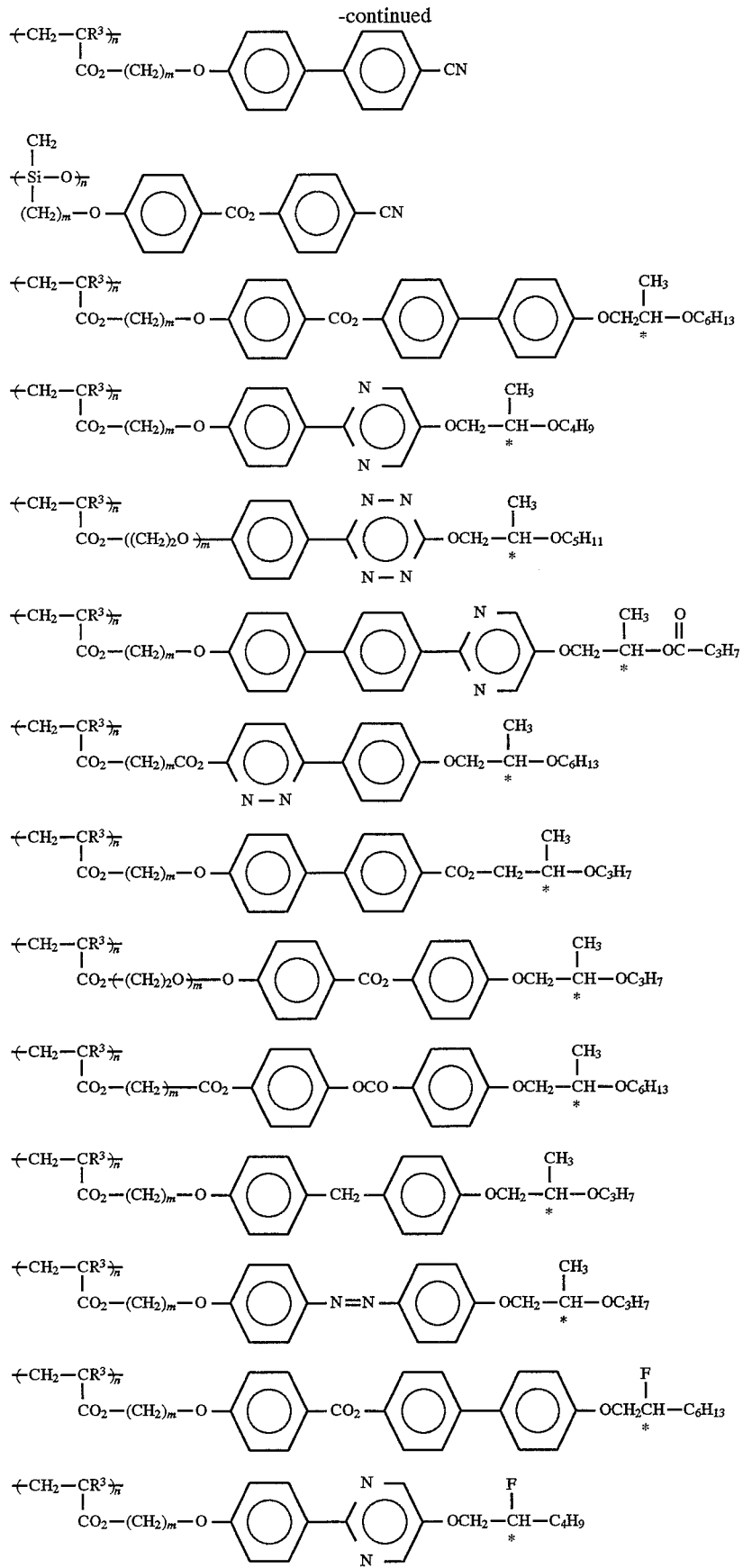

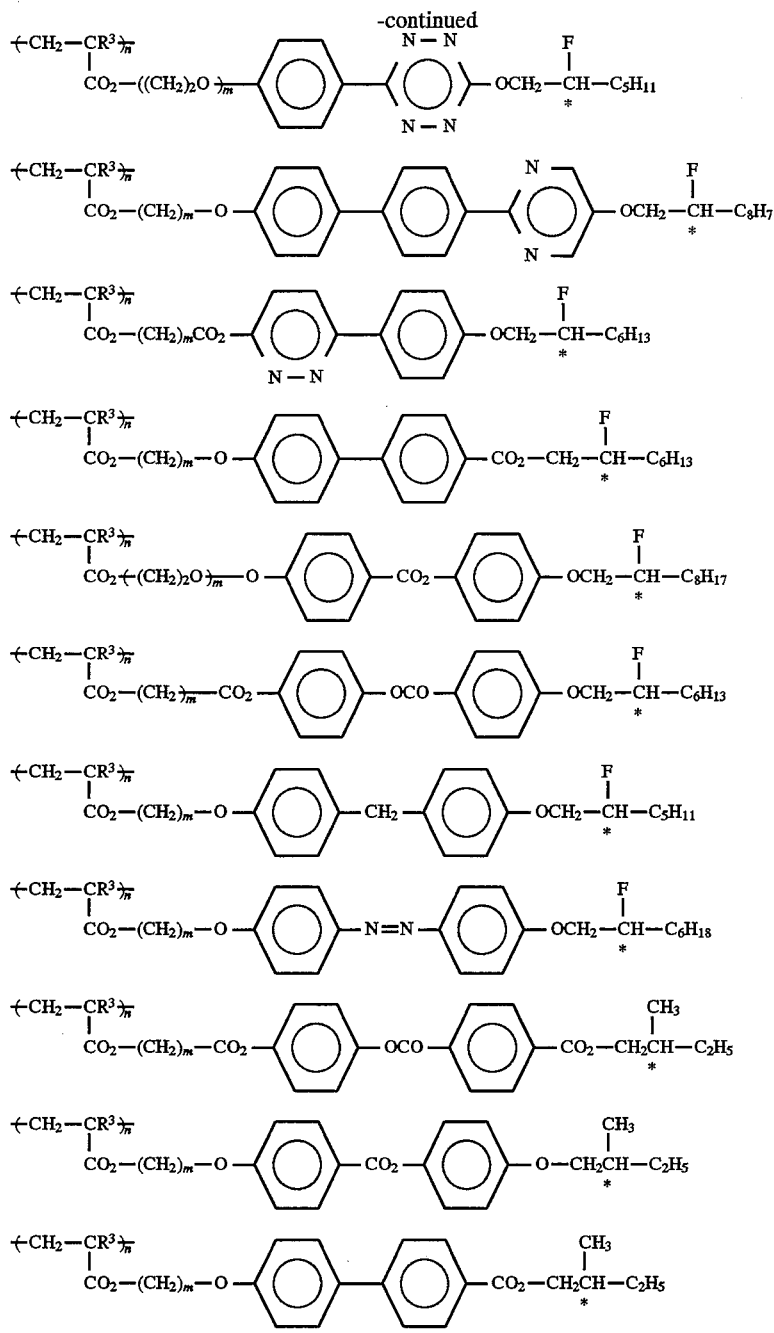
(where $R^3$ is a hydrogen atom, a alkyl group or a halogen atom and n is 3 to 10,000 and m is an integer from 0 to 20).
Furthermore, their copolymers can be used.
The low molecular liquid crystal to be blended is exemplified by:
(1)
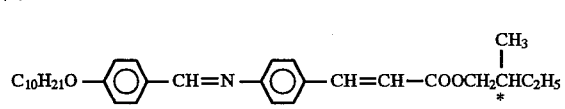
P-decyloxybendilidine-P'-amino-2-methylbutylcynnamate (DOBAMBC)
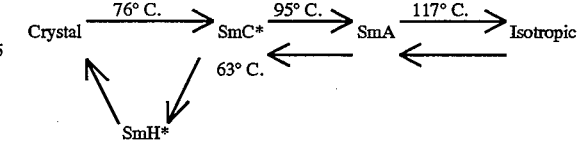
(2)
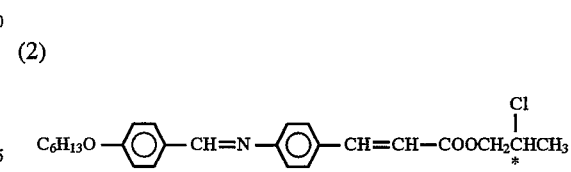

P-hexyloxybendilidine-P'-amino-2-chloropropylcynnamate (HOBACPC)

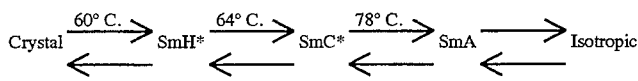

(3)

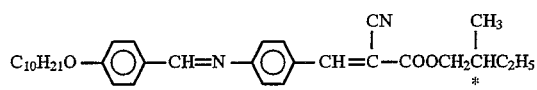

P-decyloxybendilidine-P'-amino-2-methylbutyl-α-cyanocynnamate (DOBAMBCC)

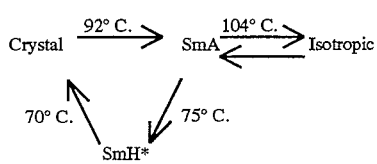

(4)

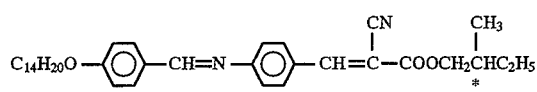

P-tetradecyloxybendilidine-P'-amino-2-methylbutyl-α-cyanocynnamate (TDOBAMBCC)

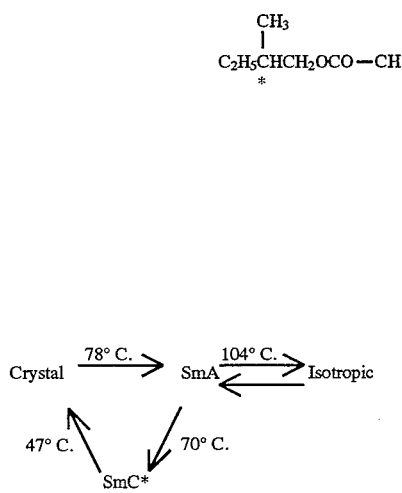

(5)

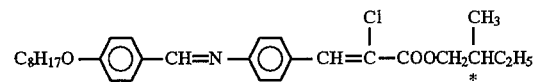

P-oxtyloxybendilidine-P'-amino-2-methylbutyl-α-chlorocynnamate (TDOBAMBCC)

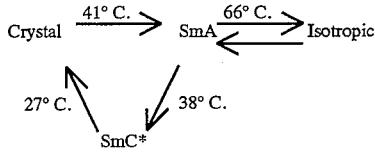

(6)

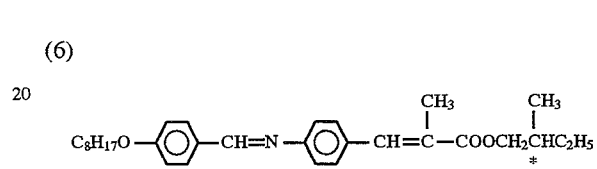

P-oxtyloxybendilidine-P'-amino-2-methylbutyl-α-methylcynnamate

Crystal ⇌ 49° C. SmC* ⇌ 58° C. SmA ⇌ 94° C. Isotropic (7)

C$_2$H$_5$CHCH$_2$OCO—CH=CH—⌬—N=N—⌬—CH=CH—COOCH$_2$CHC$_2$H$_5$
  |*                                   ↓                            |*
  CH$_3$                                O                           CH$_3$ 4,4'-azoxycynnamicacid-bis (2-methylbutyl) ester Crystal ⇌ 121° C. SmC* ⇌ 134° C. SmA ⇌ 168° C. Isotropic (8)

CH$_3$
        |
C$_2$H$_5$CHCH$_2$O—⌬—CH=N—⌬—C$_8$H$_{17}$
        *           |
                    OH 4-o-(2-methyl)-butylresolcylidine-4'-octylaniline (MBRA 8)

Crystal ⇌ 28° C. SmC* ⇌ 55° C. SmA ⇌ 62° C. Isotropic (9)

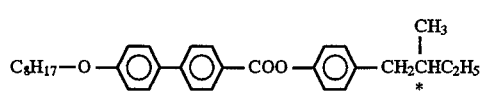

4-(2'-methylbutyl) phenyl-4'octyloxybiphenyl-4-carboxylate

Crystal ⇌ 78° C. Sm3 ⇌ 80° C. SmC* ⇌ 128.3° C. SmA ⇌ 171.0° C. Cholestric ⇌ 174.2° C. Isotropic (10)

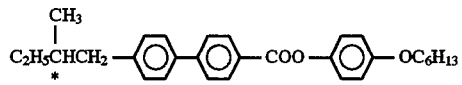

4-hexyloxyphenyl-4-(2"-methylbutyl) biphenyl-4'-carboxylate

Crystal ⇌ 68.8° C. SmC* ⇌ 80.2° C. Cholestric ⇌ 163.5° C. Isotropic (11)

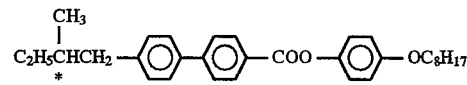

4-oxtyloxyphenyl-4-(2"-methylbutyl) biphenyl-4'-carboxylate

Crystal ⇌ 76° C. SmC* ⇌ 88.6° C. Cholestric ⇌ 154.4° C. Isotropic (12)

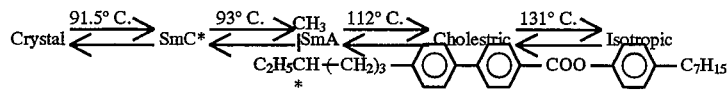

Crystal ⇌ 91.5° C. SmC* ⇌ 93° C. SmA ⇌ 112° C. Cholestric ⇌ 131° C. Isotropic 4-hexyloxyphenyl-4-(2"-methylbutyl) biphenyl-4'-carboxylate (13)

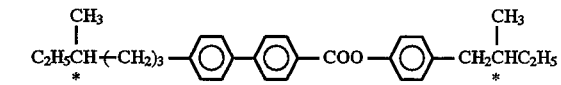

4-(2"-methylbutyl) phenyl-4-(4"-methylhexyl) biphenyl-4'-carboxylate

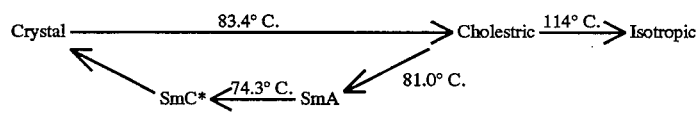

(14)

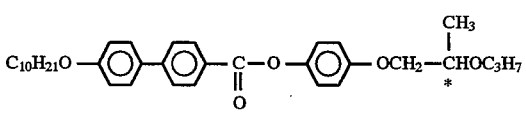

4-(2"-propyloxy) propyl) oxyphenyl-4-(decyloxy) biphenyl-4'-carboxylate

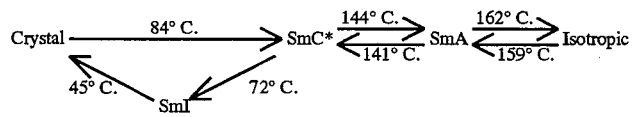

(15)

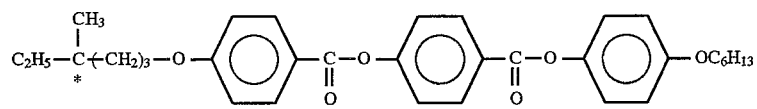

(4'-(4-hexyloxy) phenyloxycarbonyl) phenyl-p-(4"-methylhexyloxy) benzoate

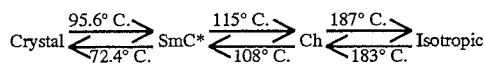

By performing blending with the aforesaid compound, the characteristics such as the temperature characteristics including the transition temperature, the viscosity characteristics, the response characteristics and the orienting characteristics can be easily controlled.

The chain polymeric liquid crystal compound according to the present invention has the aforesaid flexible spacer portion expressed by General Formula [I] and has a mesogen portion formed by a substitutable aromatic circle or an aliphatic circle. Specifically, it is exemplified by:

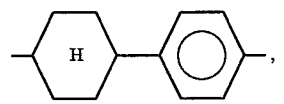

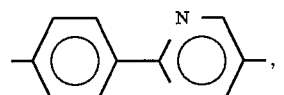

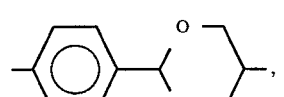

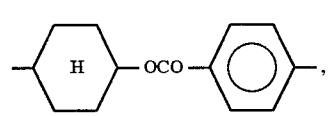

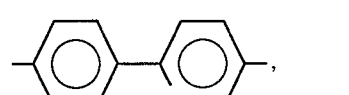

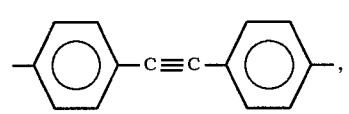

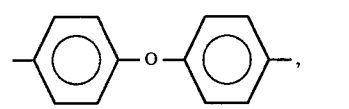

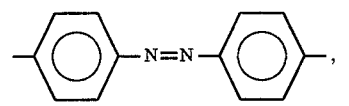

-continued

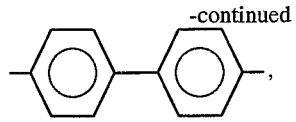

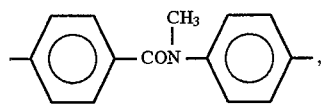

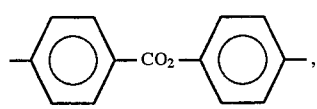

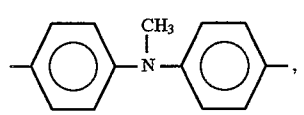

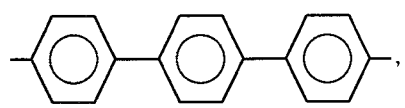

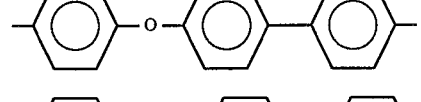

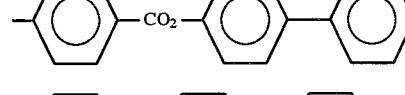

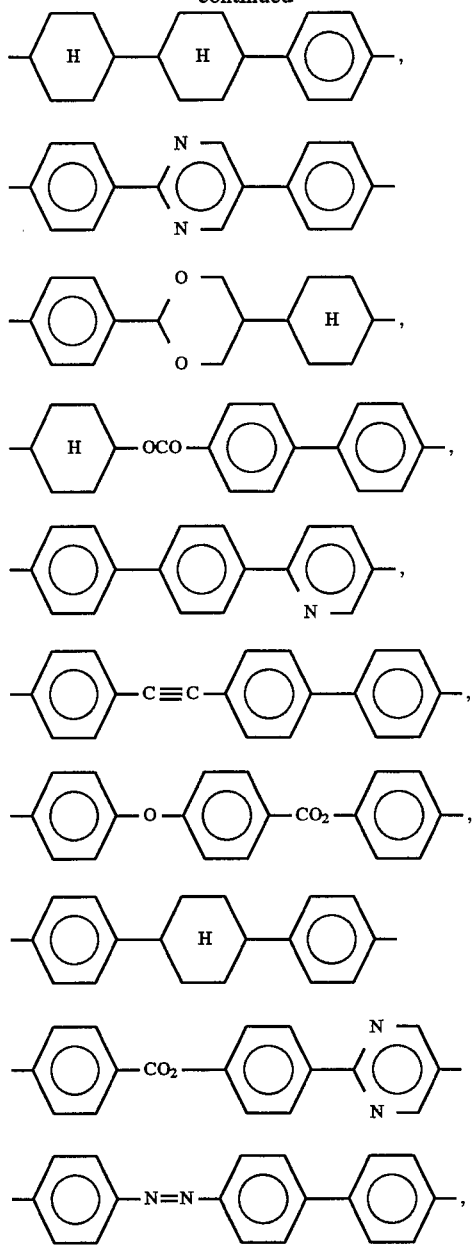

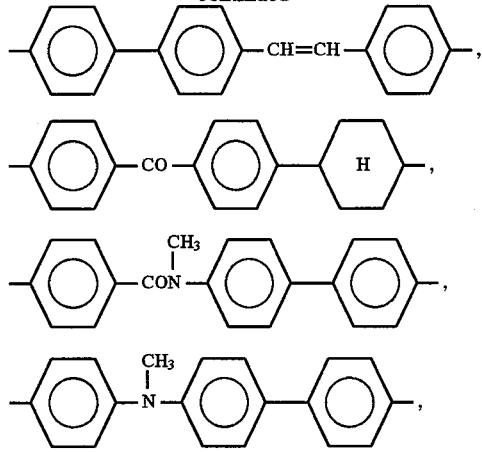

It is preferable that the mesogen portion is formed by only

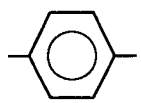

ring according to the present invention.

The chain polymeric liquid crystal compound according to the present invention has the aforesaid flexible spacer portion and the mesogen portion which are bonded by a selected bonding group (ether, ester or a carbonate bond).

In the chain polymeric liquid crystal copolymer compound according to the present invention, its flexible spacer portion, or the joint between the flexible spacer portion and the mesogen portion or the mesogen portion must contain the flexible spacer portion composed of a plurality of kinds and expressed by General Formula [I]. Furthermore, it is preferable that the chain polymeric liquid crystal copolymer compound is the polyester compound because the liquid crystal characteristics can easily be displayed.

The chain polymeric liquid crystal copolymer compound according to the present invention is composed of plural kinds of repeated units (bonding group included) each exemplified by the following materials (where n=1 to 18):

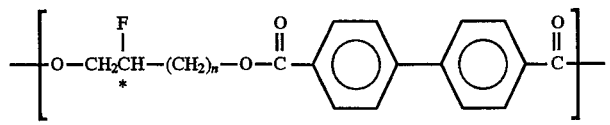

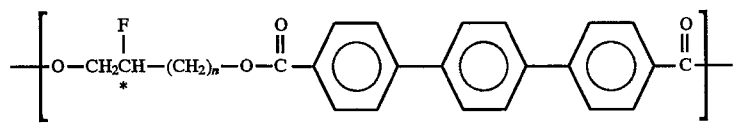

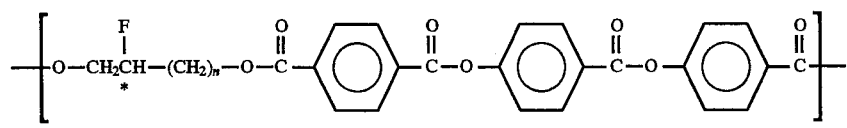

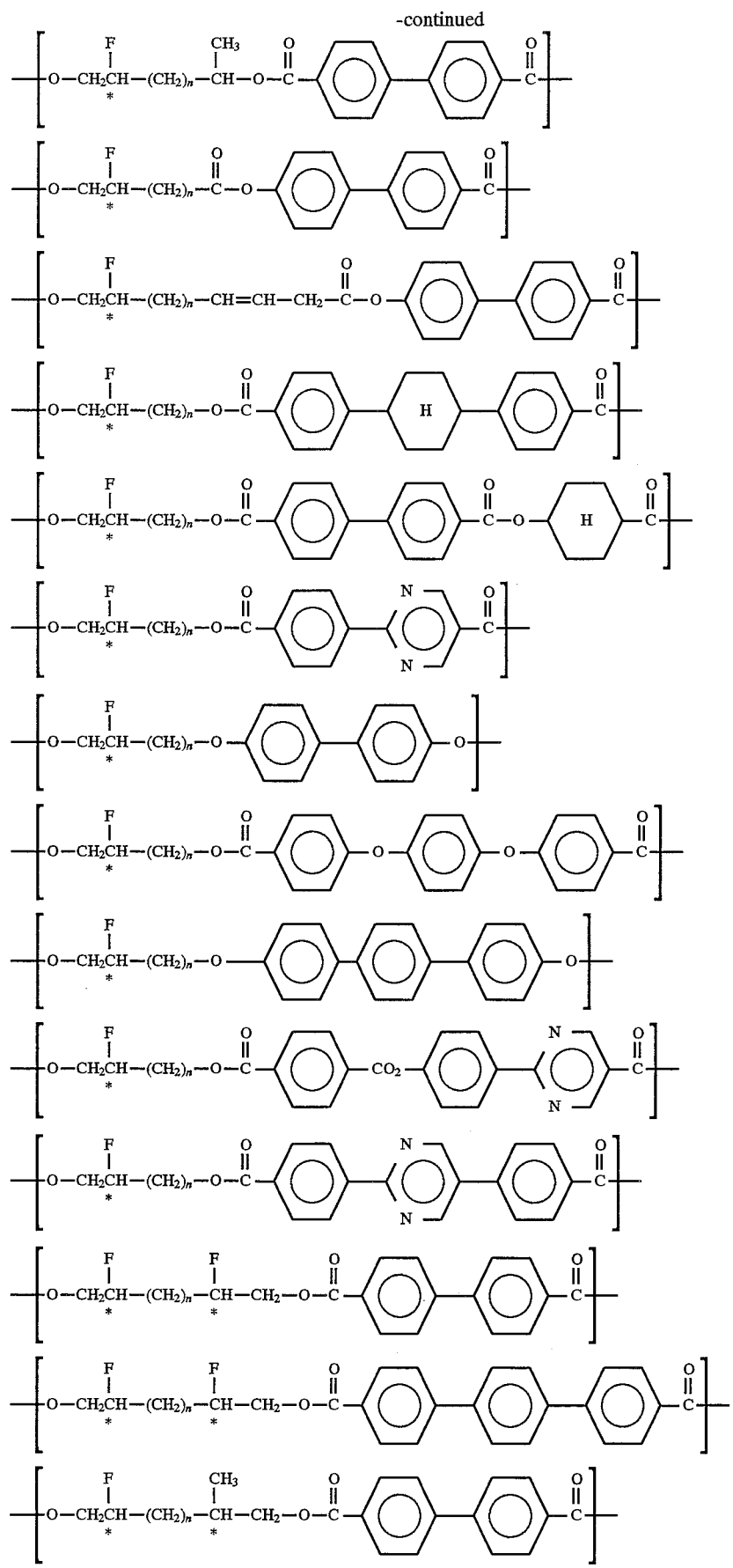

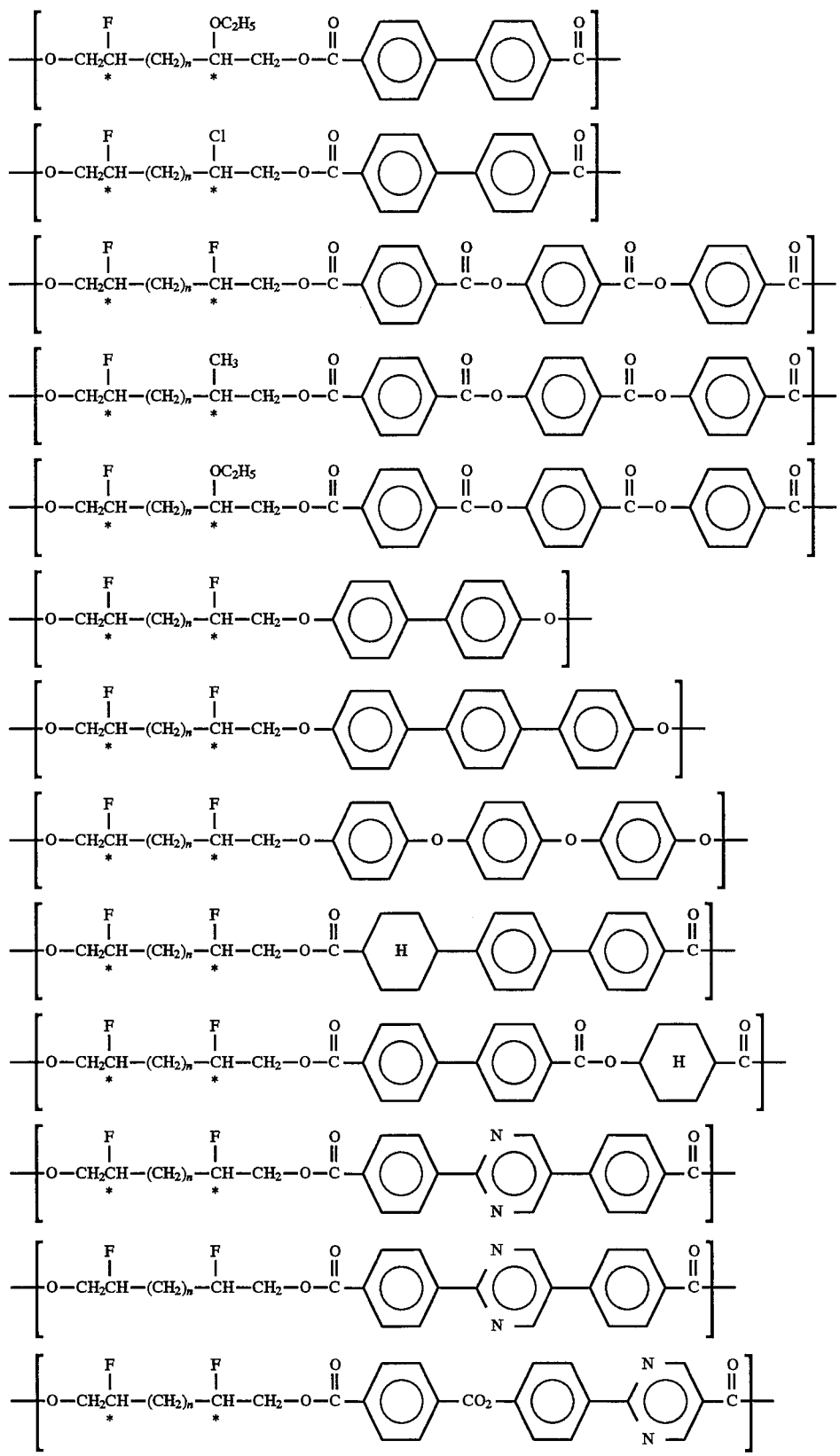
The copolymer compound may contain two or more kinds of the structural units expressed by General Formula [I]. As an alternative to this, it may be a copolymer compound containing the flexible spacer the structure of which is expressed by General Formula [I] and a flexible spacer having another structure.
The copolymer component having the flexible spacer which includes the structure except for that expressed by General Formula [I] has repeated units (bonding group included) each exemplified by the following materials:
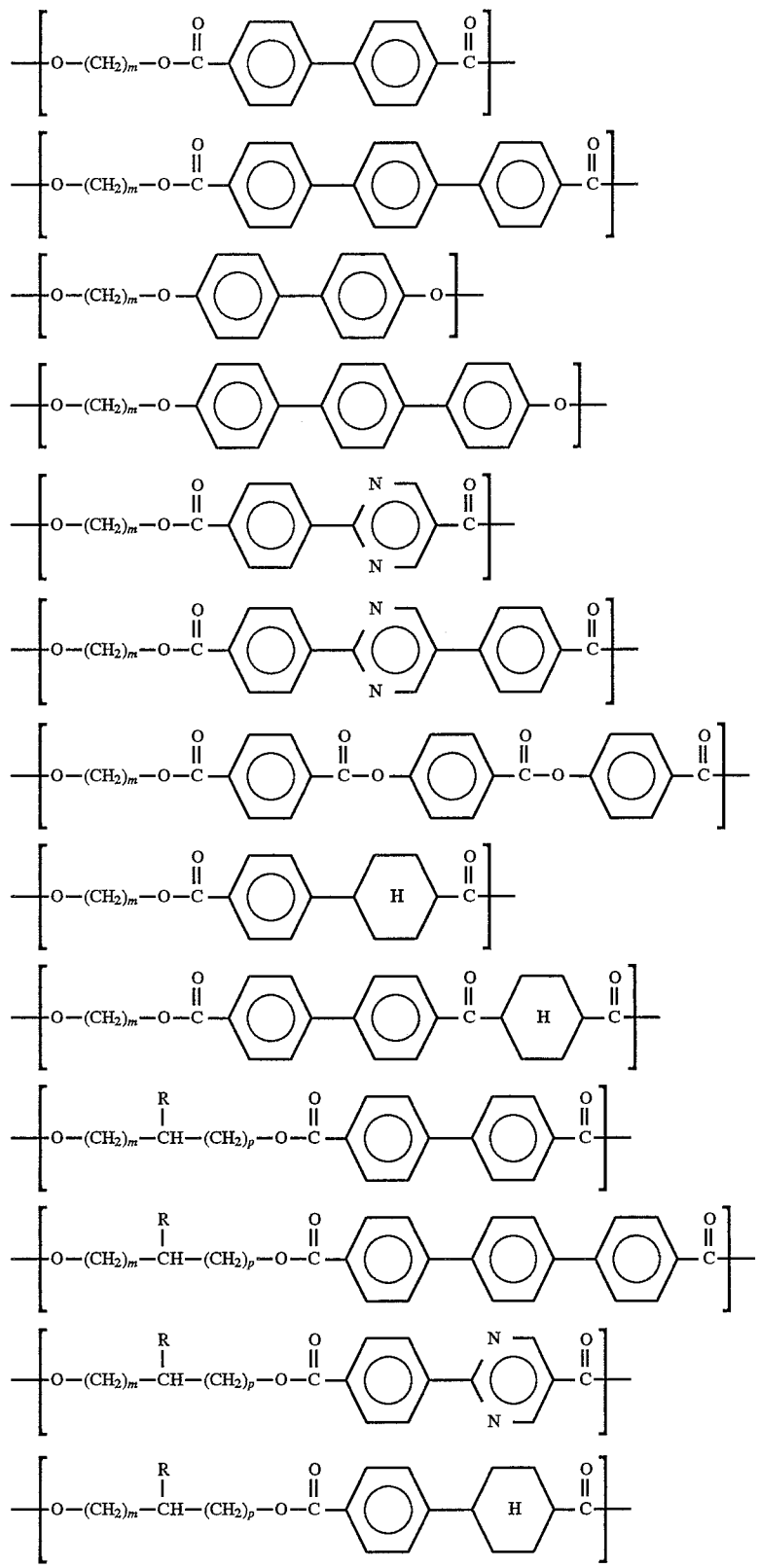

-continued

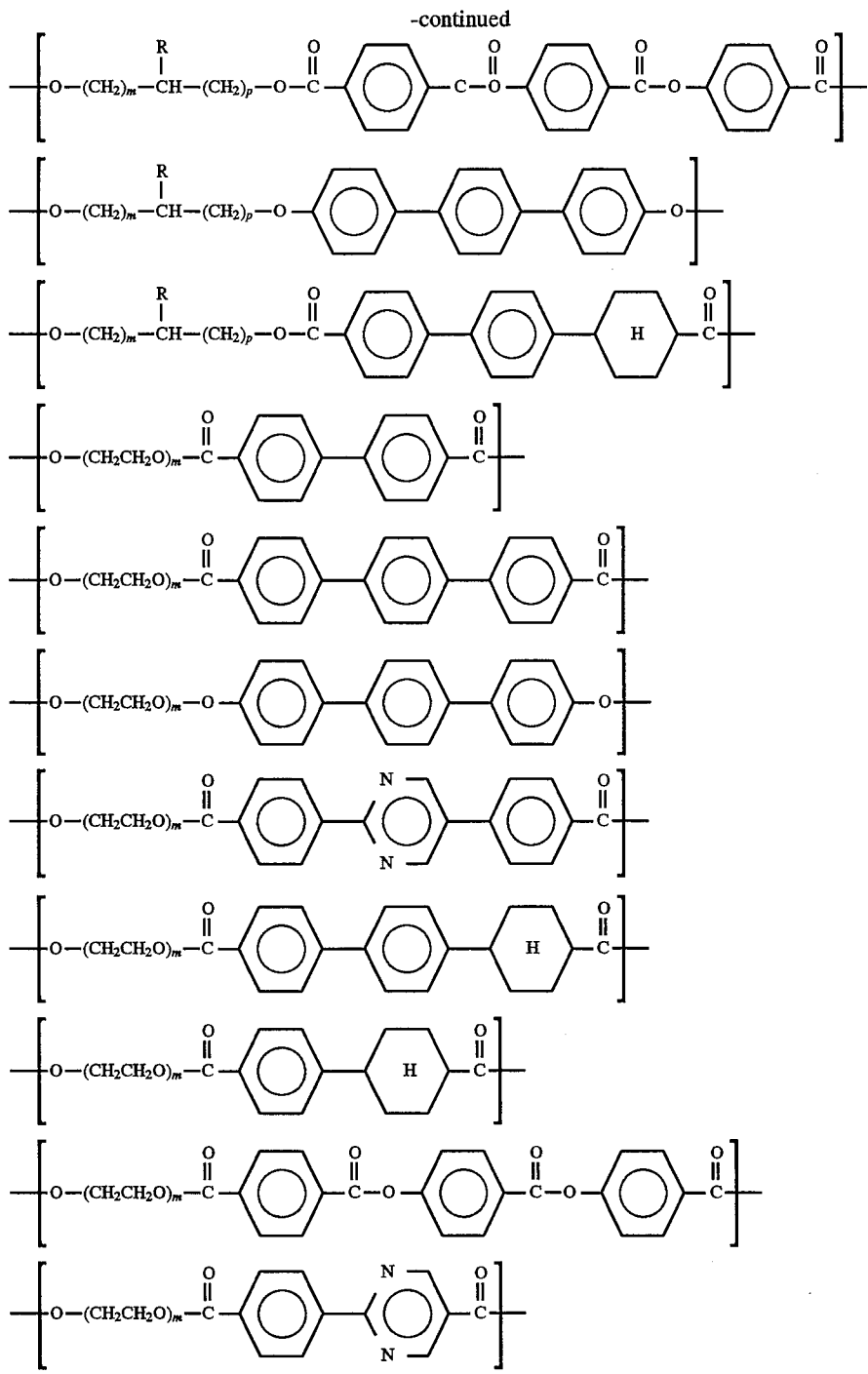

(where m and p respectively are integers 0 to 18 and R is an alkyl group, a halogen atom or an alkoxy group etc.).

The numerical average molar weight of the chain polymeric liquid crystal copolymer compound according to the present invention is 2,000 to 1,000,000, preferably 2,000 to 500,000. If it is less than 2,000, the film forming characteristic of the polymeric liquid crystal compound deteriorates, causing a problem to arise in its formability as a film formed by a coating process. If it is larger than 1,000,000, the responsiveness to the external field is deteriorated with the rise in the viscosity.

As a sole compound or a composition, the chain polymeric liquid crystal copolymer compound according to the present invention has the fluorine base having a large bipolar moment in the chiral portion thereof in a case where the chiral smectic phase having ferroelectricity is shown. Therefore, it exhibits an advantage of a very high response speed because of its large spontaneous polarization as compared with the conventional hydrocarbon type chiral group and the halogen type chiral group. Furthermore, its large intermolecular force can be enlarged due to the polarity possessed by fluorine, so that advantages can be obtained in that the liquid crystal characteristics can be displayed in a wide range and that the smectic liquid crystal phase can easily be realized.

Furthermore, the carbon-fluorine bond exhibits very significant bonding energy and thereby displays extreme stability, so that it is stable physically and chemically as compared with the halogen type chiral group.

In addition, by using the chain polymeric liquid crystal copolymer compound according to the present invention, uniform orientation, which has been very difficult to perform in the low molecular ferroelectric liquid crystal and the ferroelectric side chain type polymeric liquid crystal, can easily be performed by a stretching method or a fusion extruding method, or the like.

The composition of the chain polymeric liquid crystal copolymer compound according to the present invention can be controlled by adjusting the charge ratio of a monomer, the solvent and the polymerizing method. The physical properties of the copolymer compound can be controlled by changing the kind and the composition of the monomer, for example, the transition of the liquid crystal phase, the response characteristics and the orientation characteristics. In a case where two or more kinds of homopolymers are not mixed to each other, a copolymer having repeated units of two or more kinds may be employed, resulting in a uniform compound exhibiting the characteristics of the two materials.

A method of manufacturing the chain polymeric liquid crystal compound according to the present invention will now be described. Although it can be manufactured by a conventional method which uses polyester, or polyether, or the like, polymerization cannot proceed smoothly in a case of the polyester compound because a decomposing reaction takes place in the halogen portion due to the high temperature required in the melting polymerization method. Accordingly, the following method for manufacturing the polyester compound according to the present invention is preferably employed.

That is, a diol having dicarboxylic acid dichloride and a fluorine group is subjected to a dehydro-chlorination reaction in a solution, so that the chain polymeric liquid crystal polyester compound is manufactured. The dicarboxylic dichloride is exemplified by the following compounds:

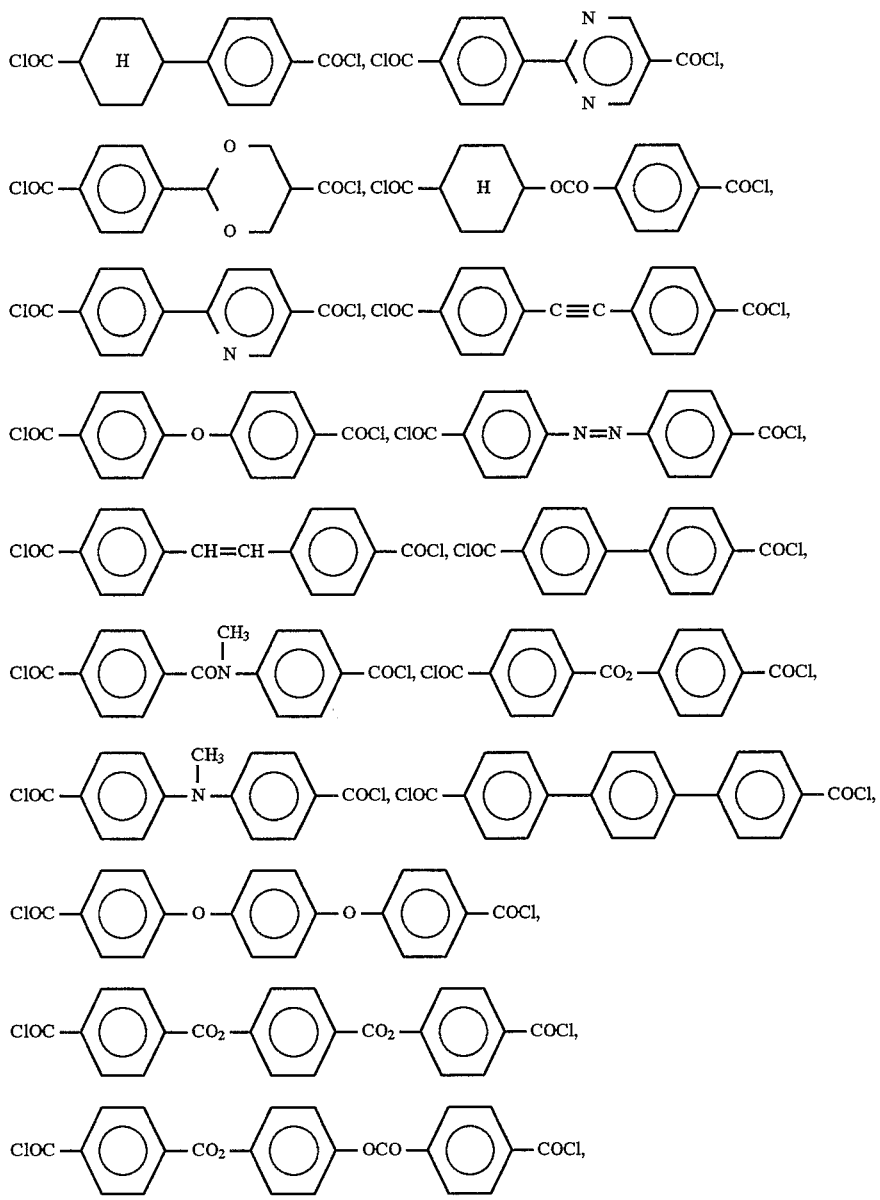

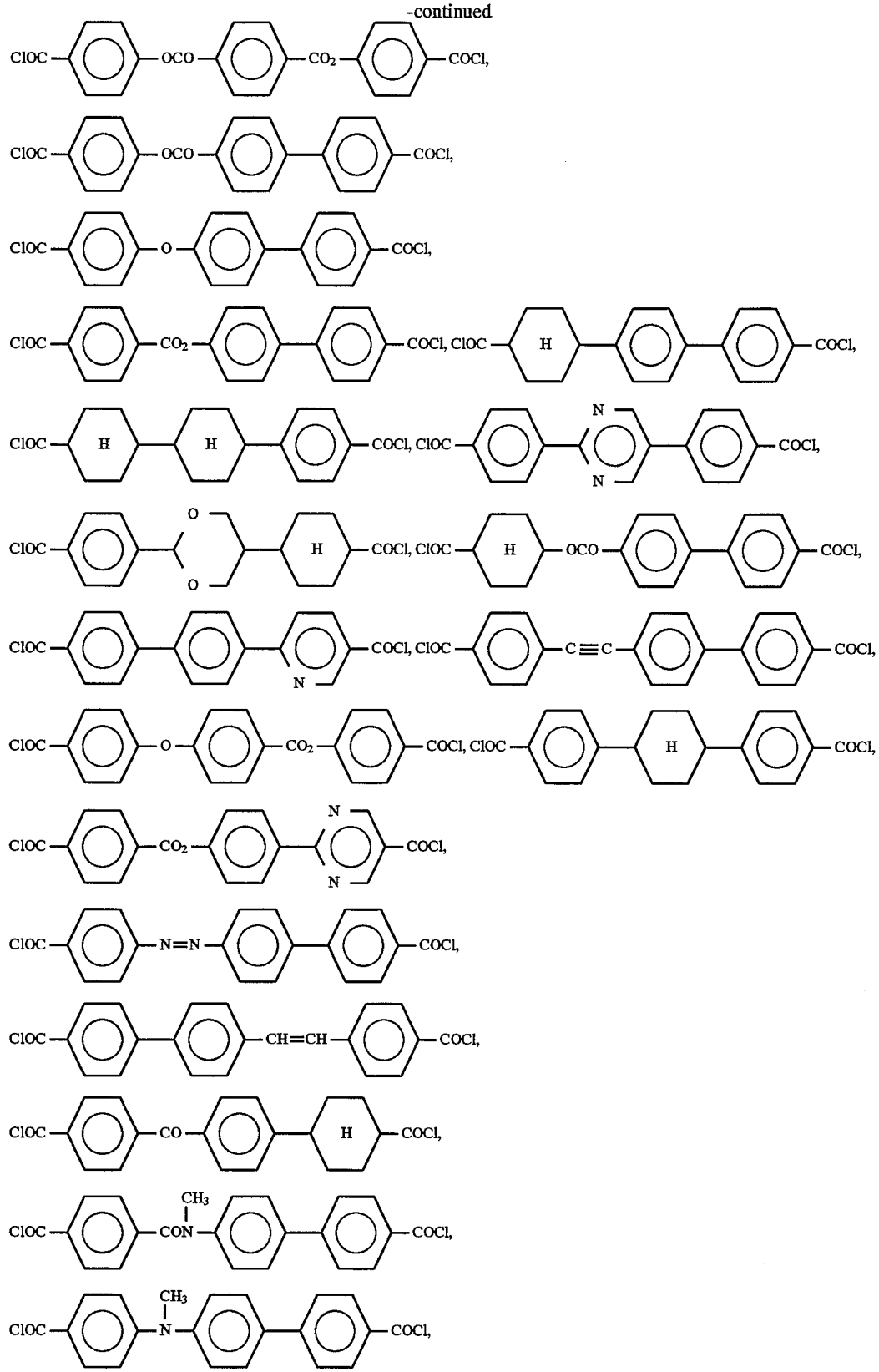

The diol is exemplified by the following compounds:

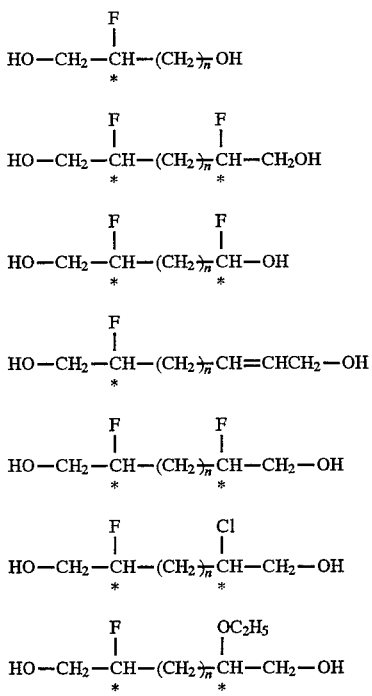

The other compound except for that expressed by General Formula [I] can be obtained by allowing the aforesaid dicarboxylic acid dichloride and the following diol to react with each other:

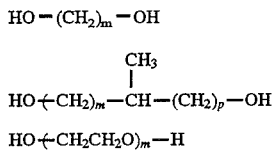

(where m and p respectively are integers from 0 to 18)

The solvent for use in the reaction must be an aprotic solvent exemplified by chloroform, benzene, toluene, DMF, DMSO, HMPA, tetrachloroethane, THF, diphenylether, and ethylene glycol dimethyl ether and the like. In order to prevent the hydrolysis of the dicarboxilyc acid dichloride by water contained in the solvent, water must be reduced from the solvent as much as possible. For the same reason, it is preferable that the reaction be carried out under an atmosphere of $N_2$, Ar, or He or the like in place of air. In order to catch hydrogen chloride, amine such as pyridine may be added to the system.

The reaction temperature must be 300° C. or lower which is lower than the boiling point of the employed solvent and to control the decomposition of the diol having the fluorine group, preferably 250° C. or lower, and still more preferably 200° C. or lower.

In order to allow the polymerizing reaction to proceed smoothly, it is preferable that the temperature be 50° C. or higher, preferably 100° C. or higher.

With the aforesaid manufacturing method, the density of the reactive base can be lowered because the reaction is performed at a low temperature and as well as the solvent reaction is employed, so that the decomposition of the diol having the fluorine group is controlled and the polymerizing reaction is allowed to smoothly proceed. As a result, polymers can easily be generated.

According to the seventh aspect of the invention, there is provided a polymeric liquid crystal composition which contains at least one of the chain polymeric liquid crystal copolymer compound according to the sixth aspect of the invention and at least one of a polymeric compound, a polymeric liquid crystal compound, a low molecular compound and a low molecular liquid crystal compound. It is preferable that a compound to be blended with the chain polymeric liquid crystal copolymer compound be polymeric liquid crystal or low molecular liquid crystal.

The polymeric liquid crystal for use in the blending process is exemplified by those aforesaid main chain polymer liquid crystal compounds shown in Chemical Materials Nos.

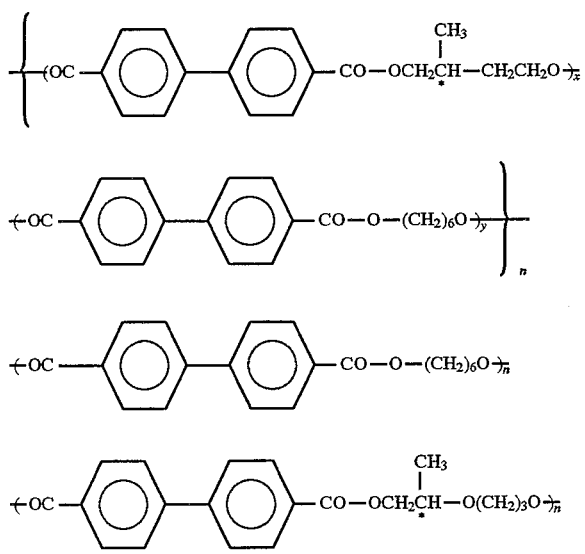

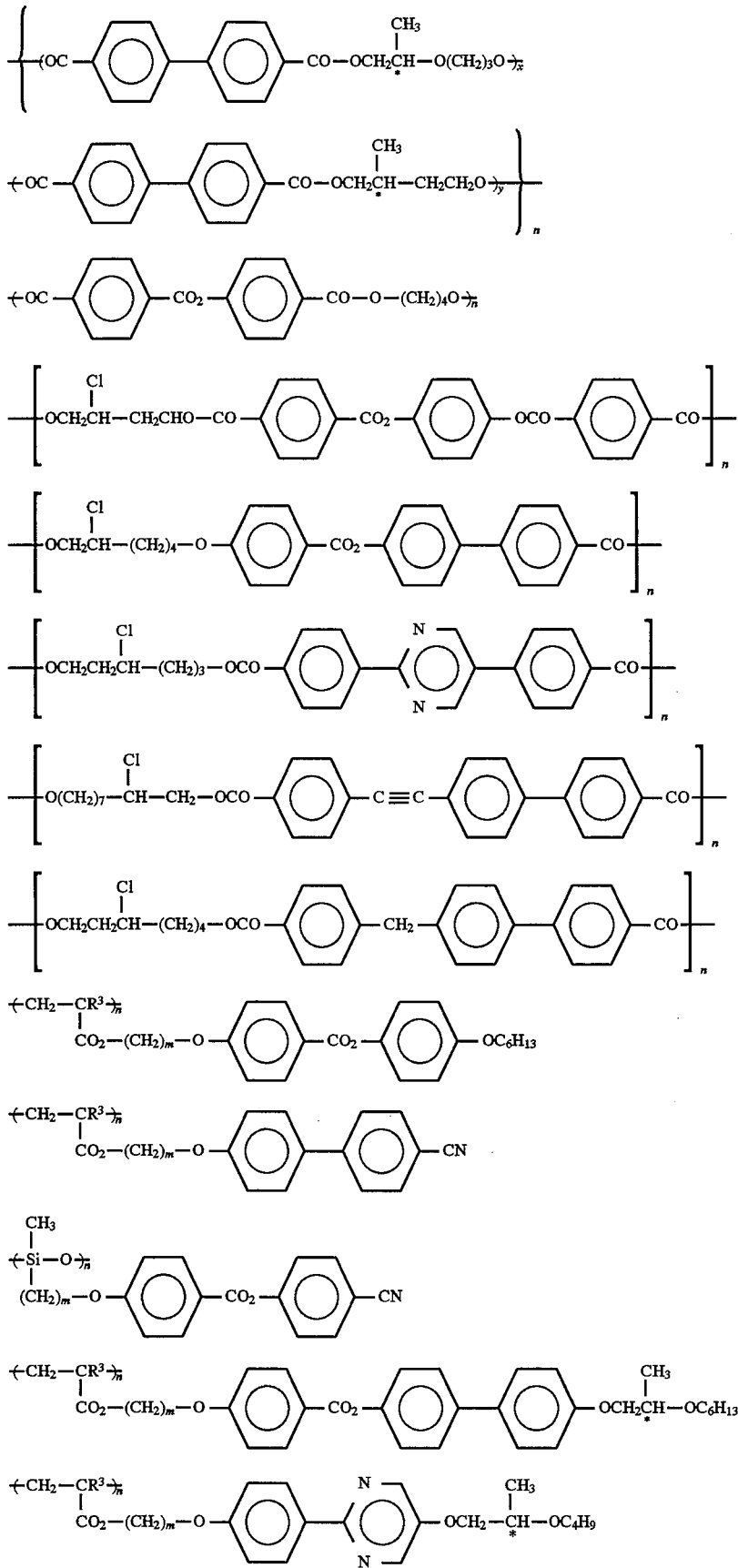

-continued
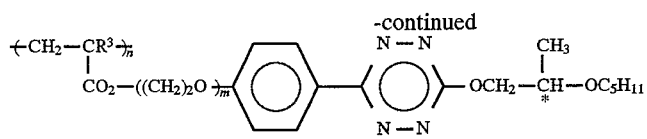
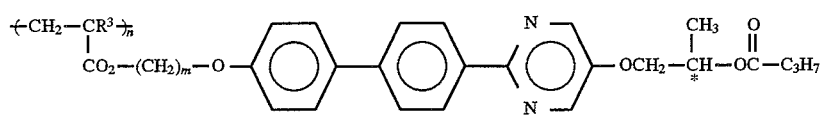
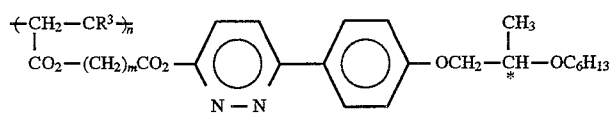
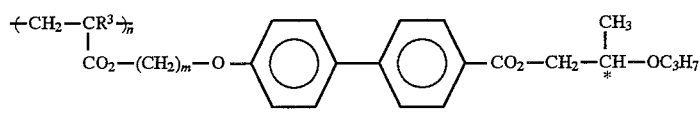
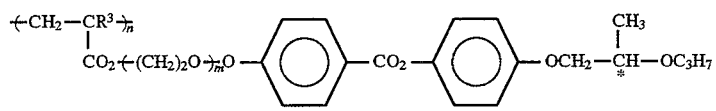
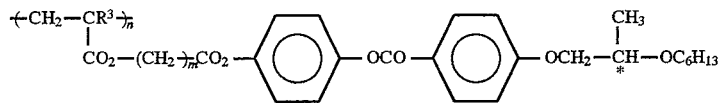
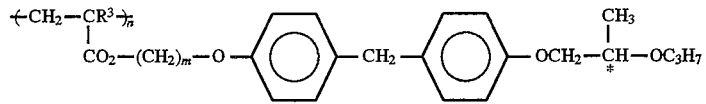
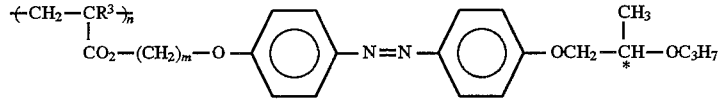
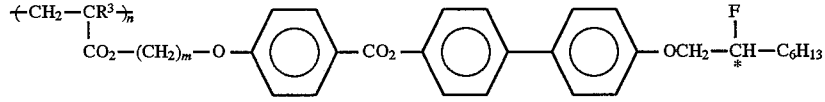
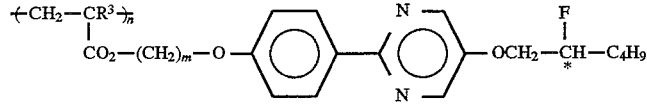
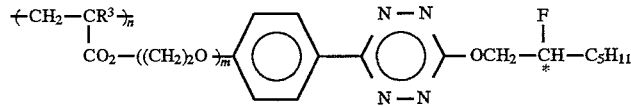
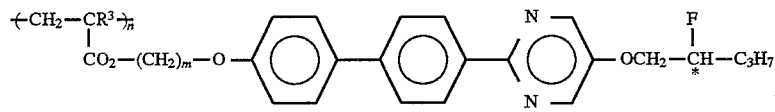
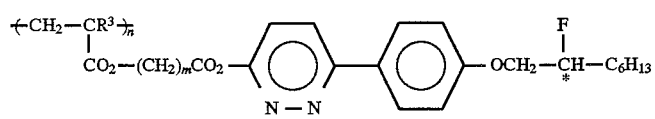
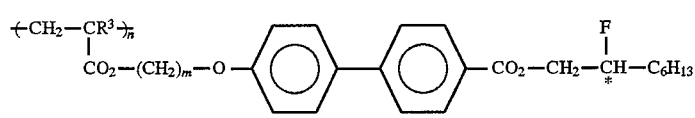

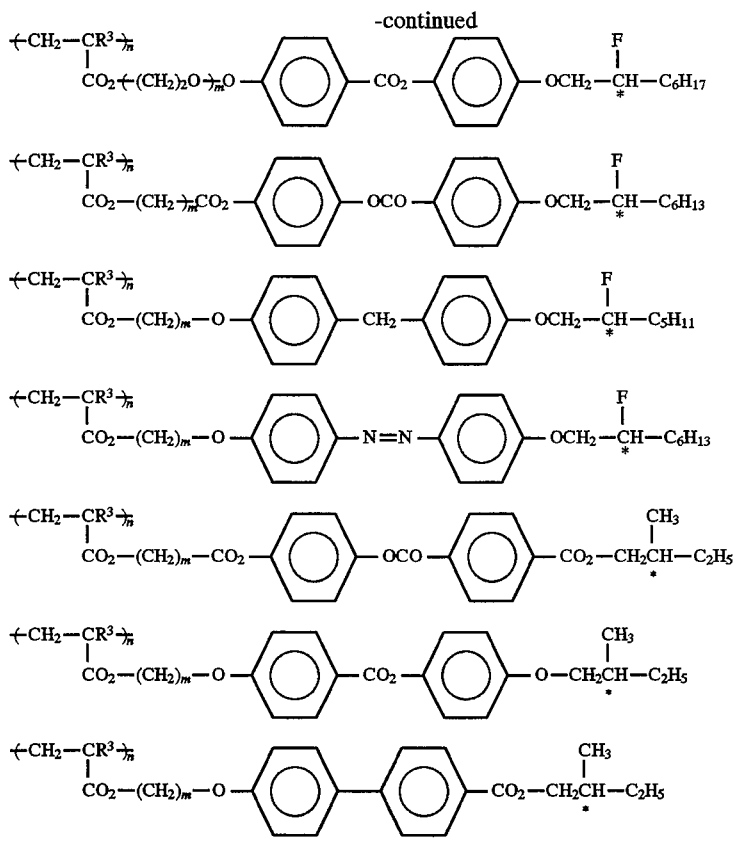

(where $R^3$ is a hydrogen atom, a alkyl group or a halogen atom and n is 3 to 10,000 and m is an integer from 0 to 20).

The low molecular liquid crystal is exemplified by the same as the aforesaid chain polymeric liquid crystal compound as shown in Chemical Materials Nos.

(1)

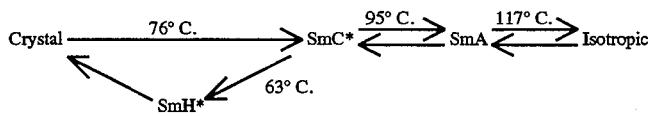

P-decyloxybendilidine-P'-amino-2-methylbutylcynnamate (DOBAMBC)

(2)

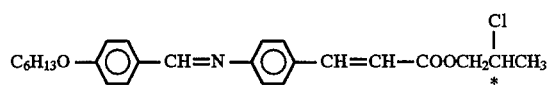

P-hexyloxybendilidine-P'-amino-2-chloropropylcynnamate (HOBACPC)

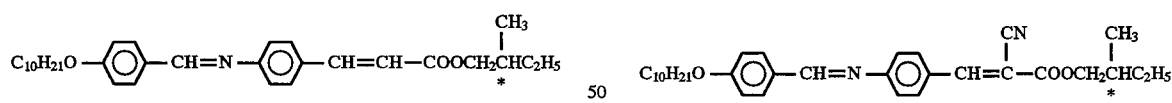

(3)

$C_{10}H_{21}O$—⟨○⟩—CH=N—⟨○⟩—CH=C(CN)—COOCH$_2$CHC$_2$H$_5$ with CH$_3$

P-decyloxybendilidine-P'-amino-2-methylbutyl-α-cyanocynnamate (DOBAMBCC)

(7)

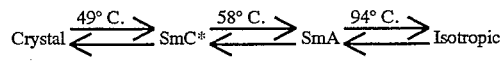

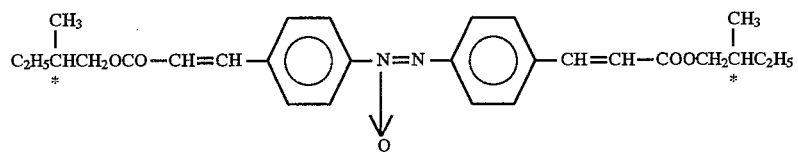

4,4'-azoxycynnamicacid-bis (2-methylbutyl) ester

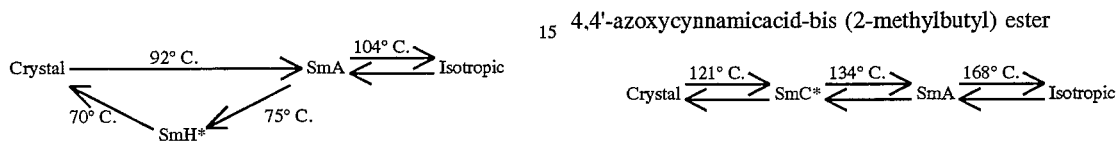

(8)

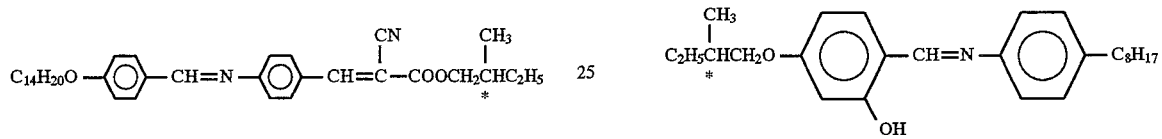

(4)

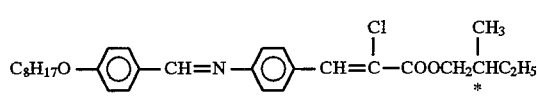

P-tetradecyloxybendilidine-P'-amino-2-methylbutyl-α-cyanocynnamate (TDOBAMBCC)

4-o-(2-methyl)-butylresolcylidine-4'-octylaniline (MBRA 8)

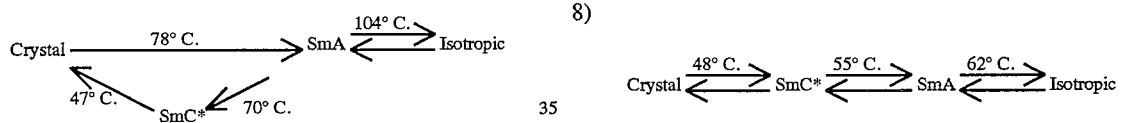

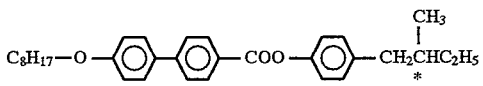

(5)

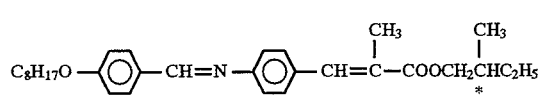

P-oxtyloxybendilidine-P'-amino-2-methylbutyl-α-chlorocynnamate (TDOBAMBCC)

(9)

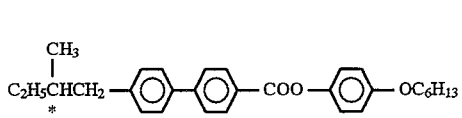

4-(2'-methylbutyl) phenyl-4'octyloxybiphenyl-4-carboxylate

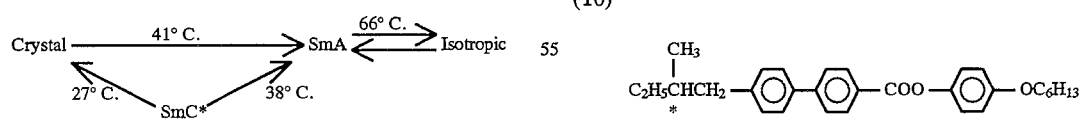

(10)

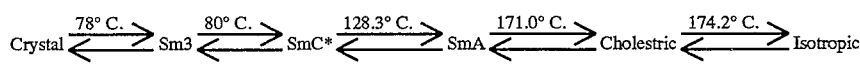

(6)

4-hexyloxyphenyl-4-(2"-methylbutyl) biphenyl-4'-carboxylate

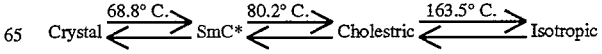

P-oxtyloxybendilidine-P'-amino-2-methylbutyl-α-methylcynnamate

(11)
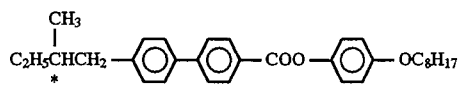
4-oxtyloxyphenyl-4-(2"-methylbutyl) biphenyl-4'-carboxylate
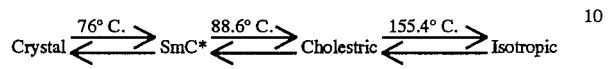
(12)
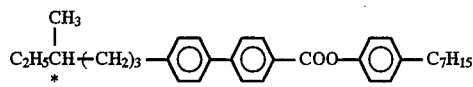
4-hexyloxyphenyl-4-(2"-methylbutyl) biphenyl-4'-carboxylate
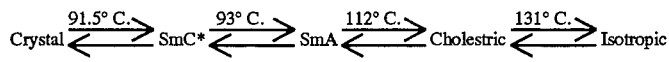
(13)
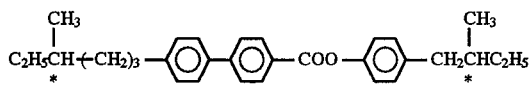
4-(2"-methylbutyl) phenyl-4-(4"-methylhexyl) biphenyl-4'-carboxylate
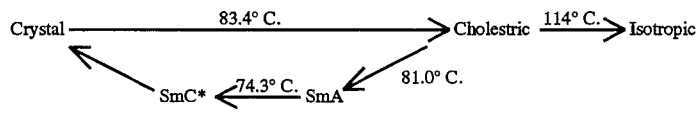
(14)
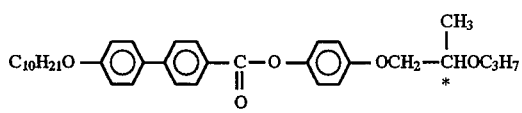
4-(2"-propyloxy) propyl) oxyphenyl-4-(decyloxy) biphenyl-4'-carboxylate
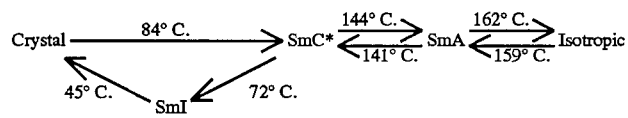

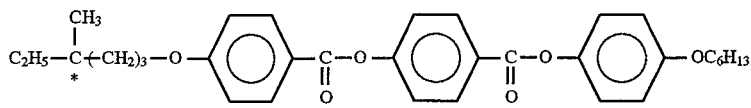

(4'-(4-hexyloxy) phenyloxycarbonyl) phenyl-p-(4"-methylhexyloxy) benzoate

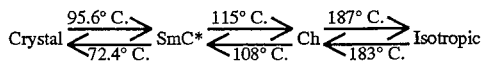

By performing blending with the aforesaid compound, characteristics such as the temperature characteristics including the transition temperature, the viscosity characteristics, the response characteristics and the orienting characteristics can be easily controlled.

The content of the chain polymeric liquid crystal compound according to the first aspect of the invention and the chain polymeric liquid crystal copolymer compound according to the sixth aspect of the invention each of which is contained in the polymeric liquid crystal composition according to the present invention is made to be 5 to 95 wt %, preferably 10 to 90 wt %. If it is less than 5 wt %, its influence, desired to cause the needed excellent responsiveness to be obtained, is unsatisfactory and the formability, the strength and film forming facility are sometimes unsatisfactory. If it is larger than 95 wt %, there is a case where the obtainable characteristics are unsatisfactory as compared with a sole compound.

It is permissible for the chain polymeric liquid crystal compound, the chain polymeric liquid crystal copolymer compound and the polymeric liquid crystal composition to contain coloring agent, light stabilizer, a plasticizer and/or a light absorber.

According to the third aspect of the invention, there is provided a polymeric liquid crystal device having polymeric liquid crystal composition which contains, as a blending component, the chain polymeric liquid crystal compound or at least one kind of the chain polymeric liquid crystal compound.

According to an eighth aspect of the invention, there is provided a polymeric liquid crystal device having the polymeric liquid crystal composition which contains, as a blending component, the chain polymeric liquid crystal copolymer compound according to the sixth aspect or at least one kind of the chain polymeric liquid crystal compound.

The polymeric liquid crystal device according to the present invention has a film formed by applying the chain polymeric liquid crystal compound, the chain polymeric liquid crystal copolymer compound or the polymeric liquid crystal composition according to the present invention to the surface of a substrate made of an arbitrary material such as glass, plastic or metal. As an alternative to this, a transparent electrode made of an ITO film or a pattern type electrode may be formed on the surface of the substrate.

Furthermore, an orienting process may be performed by a manner exemplified as follows:

(1) Horizontal Orientation (the direction of the molecular axis of the polymeric liquid crystal compound or the polymeric liquid crystal composition is oriented horizontally with respect to the surface of the substrate)

①  Rubbing Method

A film is formed on the substrate by applying a solution or by evaporating, or sputtering, the film being made of, for example, inorganic insulating material such as silicon monoxide, silicon dioxide, aluminum oxide, zirconia, magnesium fluoride, cerium oxide, cerium fluoride, silicon nitrides, silicon carbides, and boron nitrides; or organic insulating material such as polyvinyl alcohol, polyimide, polyamideimide, polyesterimide, polyparaxylene, polyester, polycarbonate, polyvinyl acetal, polyvinyl chloride, polyamide, polystyrene, cellulose resin, melamine resin, urea resin or an acrylic resin. Then, the surface is rubbed in a predetermined direction with velvet, a cloth or paper, so that an film the orientation of which is controlled is formed.

② Diagonal Evaporating Method

An oxide such a SiO, a fluoride, metal such as Au and Al, or its oxide is evaporated diagonally to the substrate to form a film the orientation of which is controlled.

③ Diagonal Etching Method

The organic or inorganic insulating film shown in 1 is etched by ion beams or oxygen plasma applied diagonally to form a film the orientation of which is controlled.

④ Use of Stretched Polymeric Film

A polymeric film made of polyester or polyvinyl alcohol or the like is stretched.

⑤ Grating Method

A photolithography, a stamper or an injection method is utilized to form a groove in the surface layer of the substrate. In this case, the polymeric liquid compound or the polymeric liquid composition is oriented in the direction of the groove.

⑥ Shearing

The polymeric liquid crystal compound or the polymeric liquid crystal composition is oriented by shearing stress applied at a temperature higher than that in a liquid crystal state.

⑦ Stretching

The orientation is made by uni- or biaxial stretching. The stretching may be performed together with the polyester or polyvinyl alcohol substrate.

(2) Vertical Orientation (the direction of the molecular axis of the polymeric liquid crystal compound or the polymeric liquid crystal composition is oriented vertically with respect to the surface of the substrate).

① A Vertically Oriented Film Formed.

A vertical oriented layer made of organic silane, lecithin or polytetrafluoroethylene or the like is formed on the substrate.

② Diagonal Evaporation

The vertical orientation can be given by selecting the evaporating angle while rotating the substrate by the diagonal evaporating method according to 1–2. The vertical orienting agent according to 1 may be applied after the diagonal evaporation has been completed.

After the orienting process has been completed as described above, a switching element or the like can be formed by providing an upper substrate having an electrode.

The polymeric liquid crystal device thus obtained is used as a display device, a storage device or the like. The polymeric liquid crystal device having the polymeric liquid crystal compound or the polymeric liquid crystal composition having the chiral smectic phase displaying ferroelectricity enables high speed switching to be performed.

Furthermore, it displays bistability, so that it can be used as a large area display device or a storage device exhibiting satisfactory memorizing performance. In order to realize the bistability, the spiral must be eliminated by a method in which the thickness of the film is reduced, specifically, to 10 µm or less.

Figure 2:
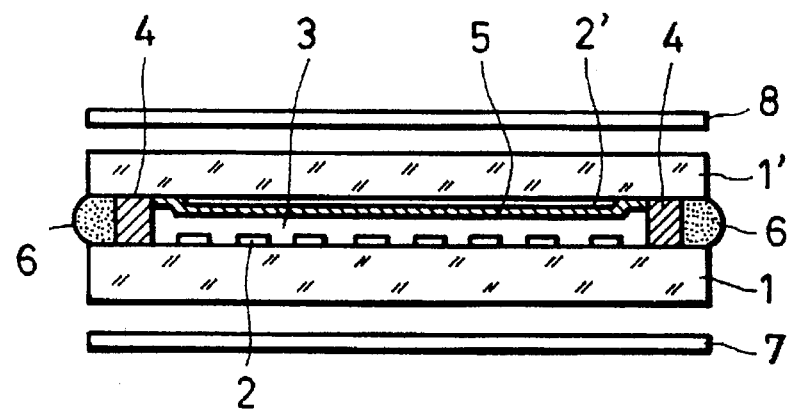
FIG. 2 is a cross sectional view taken along line AA' of FIG. 1.

An example of the liquid crystal device is shown in FIGS. 1 and 2, where FIG. 1 is a plan view which illustrates the liquid crystal device and FIG. 2 is a cross sectional view taken along line AA' of FIG. 1.

Referring to FIGS. 1 and 2, the liquid crystal device according to the present invention has a cell structure composed of a pair of substrates 1 and 1' (either of the substrates has birefringence), each made respectively of a glass plate or a plastic plate, and held at a predetermined interval by a spacer. Furthermore, in order to seal the pair of the substrates 1 and 1', an adhesive is used to adhere them. Furthermore, an electrode group (for example, a scanning voltage applying electrode group of a matrix electrode structure) composed of a plurality of transparent electrodes 2' is formed on the substrates 1' in a predetermined pattern such as an elongated pattern. In addition, an electrode group (for example, a signal voltage applying electrode group of the matrix electrode structure) composed of a plurality of reflecting layer electrodes 2 disposed to intersect the aforesaid transparent electrodes 2' is formed on the substrates 1.

The substrates 1 and 1', on which the aforesaid transparent electrodes 2 and 2 are formed, may have an orientation control film 5 formed by using, for example, inorganic insulating material such as silicon monoxide, silicon dioxide, aluminum oxide, zirconia, magnesium fluoride, cerium oxide, cerium fluoride, silicon nitrides, silicon carbides, and boron nitrides; or organic insulating material such as polyvinyl alcohol, polyimide, polyamideimide, polyesterimide, polyparaxylene, polyester, polycarbonate, polyvinyl acetal, polyvinyl chloride, polyamide, polystyrene, cellulose resin, melamine resin, urea resin or an acrylic resin.

Then, the orientation control film 5 can be obtained by forming the aforesaid inorganic insulating material or the organic insulating material before its surface is rubbed in a predetermined direction with velvet, other cloth or paper.

According to a preferable embodiment of the present invention, a film made of an inorganic insulating material such as SiO or SiO$_2$ is formed on the substrates 1 and 1' by the diagonal evaporating method, so that the orientation control film 5 is obtained.

According to another embodiment of the present invention, the surface of each of the substrates 1 and 1' made of glass or plastic or the surface of the aforesaid film made of the inorganic insulating material or the organic insulating material on each of the substrates 1 and 1' is diagonally etched, so that the surface is given the orientation control effect.

It is preferable that the aforesaid orientation control film 5 also serves as an insulating film. In order to achieve this, the thickness of the orientation control film 5 is made to be 100 Å to 1 µm, preferably 500 Å to 5000 Å. This insulating film also exhibits the advantage that generation of an electric current due to impurities contained in a display layer 3 is kept to a satisfactorily low level. Therefore, even though, operation is repeated, deterioration in the liquid crystal compound can be prevented. The liquid crystal device according to the present invention may have the orientation control films on the two sides of the substrate 1 or 1' which is positioned in contact with the display layer 3.

The reflecting layer according to the present invention may be a metal film made of Al, Au, or Ag, or the like or a ferroelectric mirror having a thickness of 0.01 to 100 µm, preferably 0.05 to 10 µm.

Figure 3:
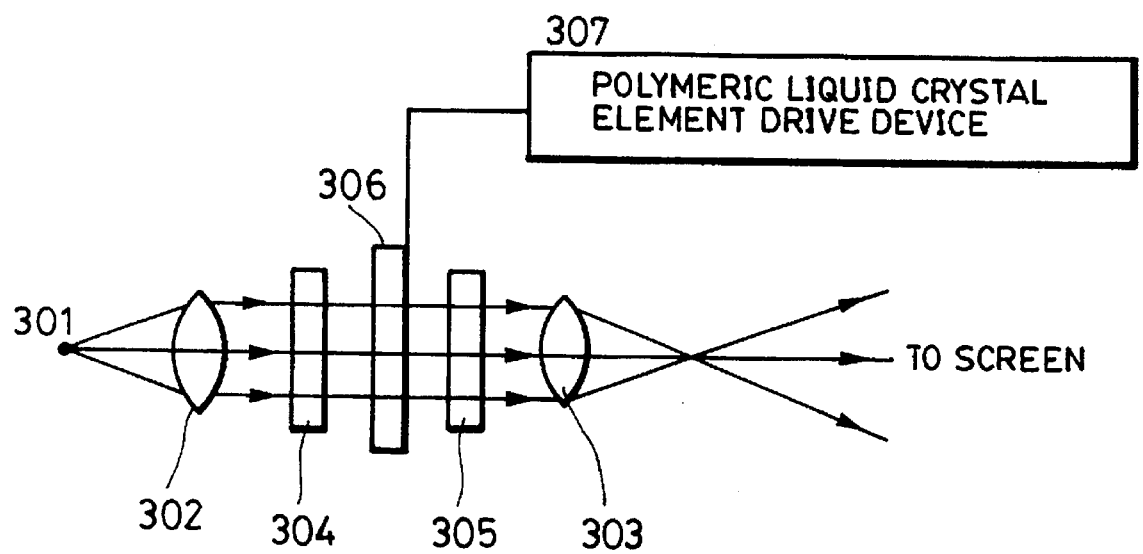
FIG. 3 illustrates an example of a display apparatus which uses the polymeric liquid crystal device according to the present invention.
Figure 4:
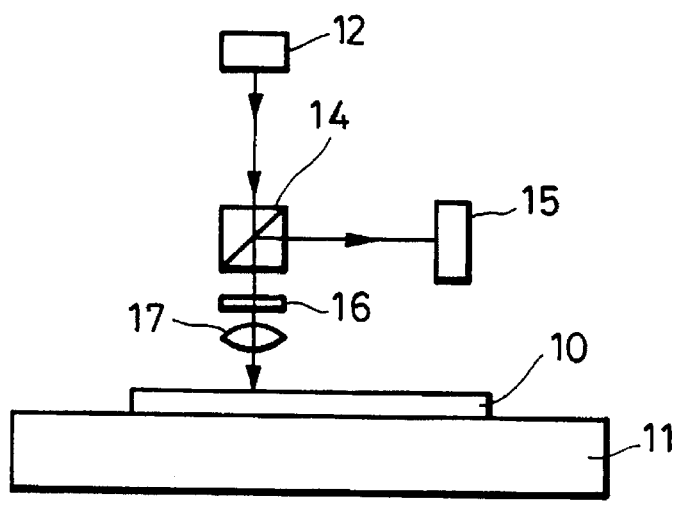
FIG. 4 illustrates an example of a recording/reproducing apparatus which uses the polymeric liquid crystal device according to the present invention.

FIG. 3 illustrates an example of the display apparatus having the liquid crystal device according to the fourth or the ninth aspect of the invention. FIG. 4 illustrates an example of a recording/reproducing apparatus which uses the liquid crystal device according to the present invention.

Referring to FIG. 3, a light beam emitted from a light source 301 and passed through the lens 302 passes through a polarizing plate 304, so that it is, as linearly polarized light, applied to a polymeric liquid crystal device 306. Then, it further passes through another polarizing plate 305 before an image of it is projected on a screen. At this time, voltage is applied to the polymeric liquid crystal device 306 by a polymeric liquid crystal drive apparatus 307, so that it is operated. For example, a color image can be obtained in a structure having a light source, an light shutter portion and a color filter to form a three-color optical image on the screen.

Referring to FIG. 4, reference numeral 10 represents an optical card including a substrate made of glass or plastic and a recording layer formed on the substrate and made of the chain polymeric liquid crystal compound, the chain polymeric liquid crystal copolymer compound or their composition according to the present invention. It is preferable that the recording layer contains a coloring material having an absorbing characteristic at the wavelength of the laser beam. Furthermore, a reflecting film made of an aluminum thin film or the like may be formed between the recording layer and the substrate. The recording layer absorbs the laser beam, so that it is converted into heat, causing a phase change, the orientation change or the shape change to be taken place by a degree of the conversion. As a result, a signal can be recorded. An electric field may be applied at this time.

The recorded data can be reproduced by detecting a reflection rate by a photodiode 15.

EXAMPLES

Examples of the present invention will now be described. However, the present invention is not limited to the following examples.

Example 1

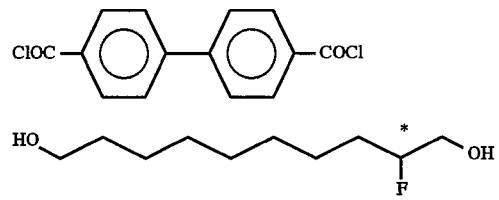

The aforesaid materials were allowed to react with each other in the amounts of 0.175 g and 0.120 g respectively in 5 ml of 1,1,2,2,-tetrachloroethane by stirring them at 150° C. for 80 hours with N$_2$ flow. After the reaction had been completed, the product was repeatedly precipitated by methanol, so that polymer a was obtained. The polymer a had $^{13}$C-NMR (in CDCl$_3$) as shown in FIG. 5.

Phase transition temperature of polymer a $$\text{chiral smetic phase} \underset{137.0°\ C.}{\overset{155.5°\ C.}{\rightleftarrows}} \text{isotropic phase}$$

Numeric average molecular weight 3,600
Weight average molecular weight 6,300
(a value obtained by converting into polyethylene by a gel permeation chromatography (GPC hereinafter))

Example 2

ClOC—◯—◯—COCl

HO—*—(chain)—*—OH
  F              F

The aforesaid materials were subjected to the process similar to Example 1 in the amounts of 0.175 g and 0.132 g respectively in 5 ml of 1,1,2,2,-tetrachloroethane, so that polymer b was obtained.

Phase transition temperature of polymer b chiral smetic phase $\xrightarrow{176.3°\ C.}$ isotropic phase
151.3° C. ↖ ↙ 157.6° C.
    cholestric phase Numeric average molecular weight 3,200
Weight average molecular weight 5,700

Example 3

ClOC—◯—◯—◯—COCl

HO—(chain)—*—OH
            F

The aforesaid materials were subjected to the process similar to Example 1 in the amounts of 0.200 g and 0.108 g respectively in 5 ml of 1,1,2,2,-tetrachloroethane, so that polymer c was obtained.

Phase transition temperature of polymer c $$\text{crystal phase} \underset{173.1°\ C.}{\overset{253.8°\ C.}{\rightleftarrows}} \text{chiral smetic phase}$$

Decomposed at about 350° C.

Numeric average molecular weight 3,000

Weight average molecular weight 5,800

Example 4

ClOC—◯—◯—◯—COCl

HO—*—(chain)—*—OH
  F              F

The aforesaid materials were subjected to the process similar to Example 1 in the amounts of 0.200 g and 0.118 g respectively in 5 ml of 1,1,2,2,-tetrachloroethane, so that polymer d was obtained.

Phase transition temperature of polymer d $$\text{crystal phase} \underset{171.5°\ C.}{\overset{250.9°\ C.}{\rightleftarrows}} \text{chiral smetic phase}$$

Decomposed at about 350° C.
Numeric average molecular weight 3,100
Weight average molecular weight 5,700

Example 5

The response speed of each of the following polymeric liquid crystal compositions to an electric field was examined, with results as shown in Table 1.

By the pressing method, the spin coating method or the casting method, the polymeric liquid crystal composition shown in Table 1 was applied to a glass plate having an ITO transparent electrode, on which the polyimide oriented film was formed, so that a film having a thickness of about 10 μm was formed. Then, annealing was performed before an electric field of 10 V/μm was applied to a liquid crystal cell having an upper electrode with the Sc*-phase. At this time, inversion of molecules corresponding to the electric field was observed.

The response speed was measured by measuring the polarization inverting current generated at the time of applying a rectangular wave.

| No. | Polymeric Liquid Crystal Composition (by weight) | Response Speed (ms) |
|---|---|---|
| 1 | a:A = 1.2:8.8 | 1.4 |
| 2 | a:B = 3.0:7.0 | 5.9 |
| 3 | b:A = 1.4:8.6 | 2.0 |
| 4 | b:B = 4.1:5.9 | 5.4 |
| 5 | c:a:A = 0.7:1.3:8.0 | 2.2 |
| 6 | d:a:B = 0.5:1.2:8.0 | 6.1 |
| 7 | a:C = 2.0:8.0 | 1.9 |
| 8 | b:A:C = 1.3:5:3.7 | 2.3 |
| 9 | a:A:C = 5.5:3.0:1.5 | 6.1 |

(note) A is the following low molecular weight liquid crystal, B and C are the following polymeric liquid crystal materials:

A:
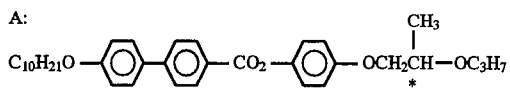

B:
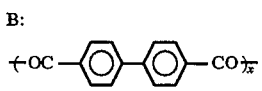

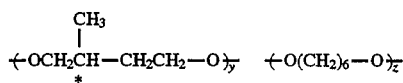

(the ratio of X, Y and Z is X:Y:Z=1.0:0.5:0.5)
Numerical average molecular weight 4,200

C:
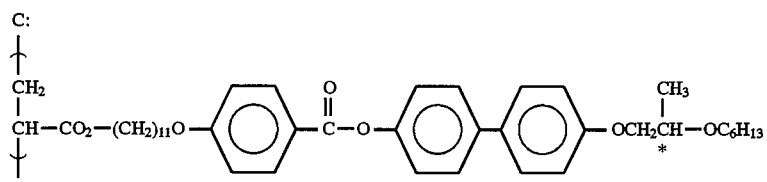

Numerical average molecular weight 7,800

Example 6

A matrix type transparent electrode was used and composition No. 2 was, similarly to Example 5, used to manufacture a polymeric liquid crystal device. The display apparatus shown in FIG. 3 was operated by using the polymeric liquid crystal device, resulting in a satisfactory image exhibiting excellent contrast to be displayed.

Example 7

The composition No. 4 according to Example 5 and the following near-infrared ray absorbing coloring material were dissolved in chloroform before the solution was applied to a PET substrate, so that an optical card was manufactured:

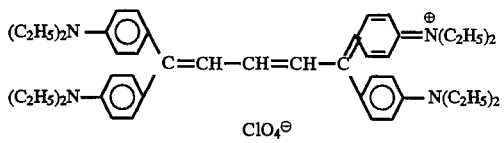

The photorecording apparatus shown in FIG. 4 was manufactured by using the optical card 4, and then recording was performed by a semiconductor laser of 780 nm. As a result, excellent recording exhibiting satisfactory contract was performed.

Example 8

The polymers a and c and the following polymer D were allowed to stand at 180° C. for 3 hours:

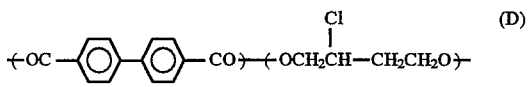

Numerical average molecular weight 4,100

The polymer D decolorized into red brown, and a gel-type decomposed material, which could not be dissolved into chloroform, was produced. On the contrary, the polymers a and c were not decolorized and no decomposition was observed.

Example 9

The response to the electric field, to which the composition No. 2 according to Example 5 was subjected, was repeated for 2 hours, resulting in no critical deterioration seen to be taking place.

Example 10

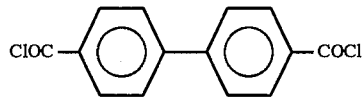

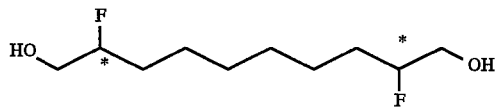

The aforesaid materials, the quantities of which were respectively 0.175 g and 0.066 g, and 0.055 g of 1,10-decanediol were allowed to react with one another in 5 ml of 1,1,2,2,-tetrachloroethane by stirring them at 150° C. for 20 hours with $N_2$ flow. After the reaction had been completed, the product was repeatedly precipitated by methanol, so that polymer e was obtained. The polymer a had $^{13}$C-NMR (in $CDCl_3$) as shown in FIG. 6.

Phase transition temperature of polymer 6.

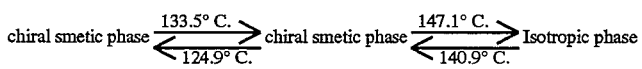

Numeric average molecular weight 3,400

Weight average molecular weight 6,000

Example 11

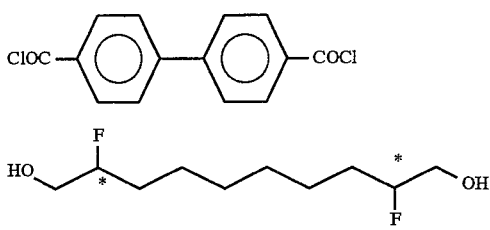

The aforesaid materials, the quantities of which were respectively 0.175 g and 0.066 g, and 0.037 g of 1,6-hexandiol were allowed to react with one another in 5 ml of 1,1,2,2,-tetrachloroethane by stirring them at 150° C. for 20 hours with $N_2$ flow. After the reaction had been completed, the product was repeatedly precipitated by methanol, so that polymer f was obtained.

Phase transition temperature of polymer f

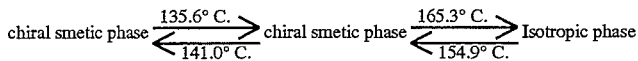

Numeric average molecular weight 3,200
Weight average molecular weight 5,900

Example 12

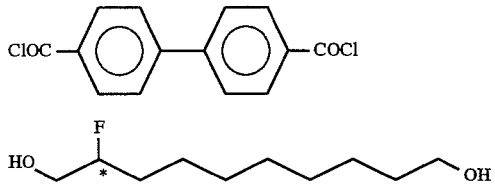

The aforesaid materials, the quantities of which were respectively 0.175 g and 0.066 g, and 0.055 g of 1,10-decandiol were allowed to react with one another in 5 ml of 1,1,2,2,-tetrachloroethane by stirring them at 150° C. for 20 hours with $N_2$ flow. After the reaction had been completed, the product was repeatedly precipitated by methanol, so that polymer g was obtained.

Phase transition temperature of polymer g

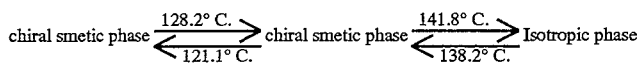

Numeric average molecular weight 3,300

Weight average molecular weight 6,300

Example 13

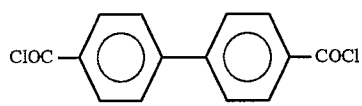

-continued

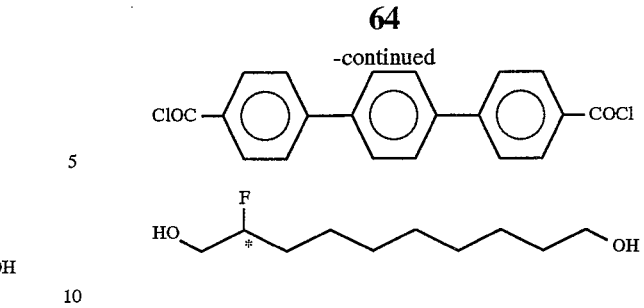

The aforesaid materials, the quantities of which were respectively 0.140 g, 0.044 g and 0.120 g, and 0.055 g, were allowed to react with one another in 5 ml of 1,1,2,2,-tetrachloroethane by stirring them at 150° C. for 20 hours with $N_2$ flow. After the reaction had been completed, the product was repeatedly precipitated by methanol, so that polymer h was obtained.

Phase transition temperature of polymer h

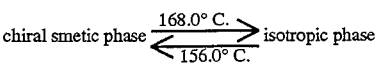

Numeric average molecular weight 3,100
Weight average molecular weight 5,700

Example 14

The response speed of each of the following polymeric liquid crystal compositions to an electric field was examined, with results as shown in Table 2.

By the pressing method, the spin coating method or the casting method, the polymeric liquid crystal composition shown in Table 2 was applied to a glass plate having an ITO transparent electrode, on which the polyimide oriented film was formed, so that a film having a thickness of about 10 µm was formed. Then, annealing was performed before an electric field of 10 V/µm was applied to a liquid crystal cell having an upper electrode with the Sc*-phase. At this time, inversion of molecules corresponding to the electric field was observed.

The response speed was measured by measuring the polarization inverting current generated at the time of applying a rectangular wave.

| No. | Polymeric Liquid Crystal Composition (by weight) | Response Speed (ms) |
|---|---|---|
| 10 | e:A = 3.0:7.0 | 2.7 |
| 11 | e:B = 2.0:8.0 | 6.3 |
| 12 | e:C = 1.2:8.8 | 2.8 |
| 13 | f:A = 2.1:7.9 | 1.9 |
| 14 | f:B = 1.2:8.8 | 5.8 |
| 15 | g:A = 2.2:7.8 | 2.2 |

-continued

| No. | Polymeric Liquid Crystal Composition (by weight) | Response Speed (ms) |
|---|---|---|
| 16 | g:B = 3.4:6.6 | 5.5 |
| 17 | g:A:B = 0.7:7.5:1.8 | 3.1 |
| 18 | h:A:B = 0.5:8.0:1.5 | 3.0 |
| 19 | e:A:B = 5.6:2.3:2.1 | 6.1 |

(note) A is the following low molecular weight liquid crystal, B and C are the following polymeric liquid crystal materials:

A:

$C_{10}H_{21}O$—⟨O⟩—⟨O⟩—$CO_2$—⟨O⟩—$OCH_2\overset{*}{C}H$—$OC_3H_7$
                                                    |
                                                    $CH_3$

B:

$+OC$—⟨O⟩—⟨O⟩—$CO+_x$ $+OCH_2\overset{*}{C}H$—$CH_2CH_2$—$O+_y$   $+O(CH_2)_6$—$O+_z$
         |
         $CH_3$ (the ratio of X, Y and Z is X:Y:Z=1.0:0.5:0.5)
Numerical average molecular weight 4,200

C:

$+CH_2$
  |
  $CH$—$CO_2$—$(CH_2)_{11}O$—⟨O⟩—$\overset{O}{\underset{\|}{C}}$—$O$—⟨O⟩—⟨O⟩—$OCH_2\overset{*}{C}H$—$OC_6H_{13}$
                                                                            |
                                                                            $CH_3$ Numerical average molecular weight 7,800

Example 15

A matrix type transparent electrode was used and composition No. 11 was, similarly to Example 14, used to manufacture a polymeric liquid crystal device. The display apparatus shown in FIG. 3 was operated by using the polymeric liquid crystal device, resulting in a satisfactory image exhibiting excellent contrast to be displayed.

Example 16

The composition No. 14 according to Example 14 and the following near infrared ray absorbing coloring material were dissolved in chloroform before the solution was applied to a PET substrate, so that an optical card was manufactured.

$(C_2H_5)_2N$—⟨O⟩
              \
               C=CH—CH=CH—C⟨⟩=N(C_2H_5)_2 · $ClO_4^\ominus$
              /                    ⟨O⟩—$N(C_2H_5)_2$
$(C_2H_5)_2N$—⟨O⟩

The photorecording apparatus shown in FIG. 4 was manufactured by using the optical card 4, and then recording was performed by a semiconductor laser of 780 nm. As a result, excellent recording exhibiting satisfactory contract was performed.

Example 17

The polymers e and g and the following polymer D were allowed to stand at 180° C. for 3 hours.

$+OC$—⟨O⟩—⟨O⟩—$CO+$—$+OCH_2\overset{Cl}{\underset{|}{C}H}$—$CH_2CH_2O+$   (D)

Numerical average molecular weight 4,100

The polymer D decolorized into red brown, and a gel-type decomposed material, which could not be dissolved into chloroform, was produced. On the contrary, the polymers e and g were not decolorized and no decomposition was observed.

Example 18

The response to the electric field, to which the composition No. 2 according to Example 5 was subjected, was repeated for 2 hours, resulting in no critical deterioration seen to be taking place.

Examples 19 to 22

HO~~~~~~~~$\overset{*}{C}$H~OH  and
              |
              F

ClOC—⟨O⟩—$CO_2$—⟨O⟩—COCl obtained in Example 1, polymer was obtained similarly to Example 1 (polymer i).

By using

HO~~~~~~~~~$\overset{*}{C}$H~OH and
               |
               F

ClOC—⟨O⟩—$CO_2$—⟨O⟩—⟨O⟩—COCl, polymer was obtained (polymer j).

By using

HO~$\overset{*}{C}$H~~~~~~~$\overset{*}{C}$H~OH and
    |              |
    F              F ClOC—⟨O⟩—$CO_2$—⟨O⟩—OCO—⟨O⟩—COCl obtained in Example 2, polymer was obtained (polymer k).

By using

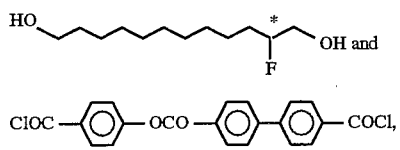

polymer was obtained (polymer l).

Each of the aforesaid polymers shows liquid crystal characteristic.

Experiments were performed while replacing polymer a according to Example 6 by the aforesaid polymers i to e, resulting in a satisfactory display which exhibits excellent contrast.

Examples 23 to 27

Under the same conditions as those of Example 11 except for a fact that

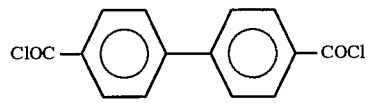

is replaced by

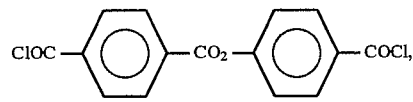

polymer was obtained (polymer m).

Under the same conditions as those of Example 12 except for a fact that

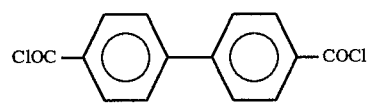

is replaced by

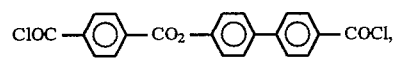

polymer was obtained (polymer n).

Under the same conditions as those of Example 11 except for a fact that

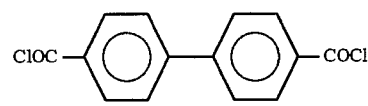

is replaced by

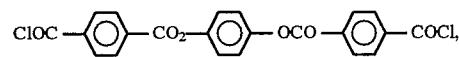

polymer was obtained (polymer o).

Under the same conditions as those of Example 13 except for a fact that

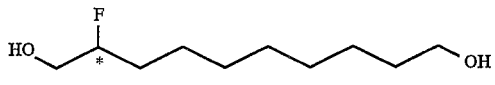

is replaced by

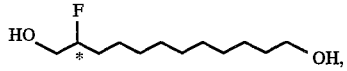

polymer was obtained (polymer p).

Under the same conditions as those of Example 13 except for a fact that

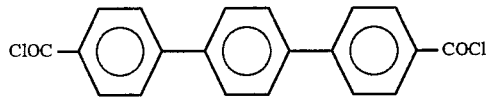

is replaced by

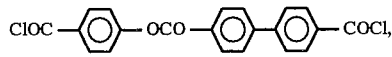

polymer was obtained (polymer q).

Each of the aforesaid polymers shows liquid crystal characteristic.

Experiments were performed while replacing polymer e according to Example 15 by the aforesaid polymers m to q, resulting in a satisfactory display which exhibits excellent contrast.

As described above, according to the present invention, the optoelectronic device such as a display or a memory or the like having a larger area can be easily realized by utilizing the characteristics of the polymer. Furthermore, since the fluorine group is included in the flexible spacer portion, the liquid crystal temperature range is satisfactorily large. Furthermore, in a case where ferroelectric characteristics are possessed as a compound or a composition, a large spontaneous polarization is realized due to the large dipole of the fluorine group. Therefore, the chain polymeric liquid crystal compound and the polymeric liquid crystal composition exhibiting excellent responsibility as compared with the conventional chain polymeric liquid crystal compound and the polymeric liquid crystal composition can be obtained.

According to the present invention, the optoelectronic device such as a display or a memory or the like having a larger area can be easily realized by utilizing the characteristics of the polymer. Furthermore, since the fluorine group is included in the flexible spacer portion, a liquid crystal temperature range is satisfactorily large. Furthermore, in a case where ferroelectric characteristics is possessed as a compound or a composition, a large spontaneous polarization is realized due to a large dipole of the fluorine group. Therefore, the chain polymeric liquid crystal copolymer compound and the polymeric liquid crystal composition exhibiting excellent responsibility as compared with the conventional chain polymeric liquid crystal compound and the polymeric liquid crystal composition can be obtained.

The chain polymeric liquid crystal copolymer compound according to the present invention has plural kinds of repetition units. Therefore, the characteristics of each of the repetition unit structure can be possessed and as well as their physical properties can be controlled.

According to the present invention, a novel and excellent liquid crystal device, apparatus and method of using it can be provided by using the chain polymeric liquid crystal compound, the chain polymeric liquid crystal copolymer and the polymeric liquid crystal composition.

Although the invention has been described in its preferred forms with a certain degree of particularly, it is understood that the present disclosure of the preferred form has been changed in the details of construction and the combination and arrangement of parts may be resorted to without departing from the spirit and the scope of the invention as hereinafter claimed.

What is claimed is:

1. A chain polymeric liquid crystal compound comprising a mesogen portion and a structure expressed by the following general formula (I) as a flexible spacer:

$$\text{General Formula (I)}$$
$$+X-Y-\overset{F}{\underset{*}{\overset{|}{C}H}}-CH_2-O+$$

(wherein X is —O—, —O—CH$_2$—CH$_2$—, —O—CH$_2$—, $$-O-\underset{\underset{O}{\|}}{C}-, -O-CH_2-CH=CH-,$$

$$-O-\overset{CH_3}{\underset{|}{C}H}- \text{ or } -O-CH_2-\overset{Z}{\underset{*}{\overset{|}{C}H}}-,$$

Y is —(CH$_2$)$_n$— (n=1 to 18), Z is a halogen atom, an alkyl group or an alkoxy group, and * is an asymmetric carbon atom).

2. A chain polymeric liquid crystal polyester compound comprising a structure according to claim 1 and expressed by general formula [I] as a flexible spacer.

3. A polymeric liquid crystal device containing at least one chain polymeric liquid crystal compound according to claim 1 or 2.

4. An apparatus compromising a polymeric liquid crystal device according to claim 3.

5. A chain polymeric liquid crystal compound according to claim 1, which has a numerical average molecular weight in the range of 2,000 to 1,000,000.

6. A chain polymeric liquid crystal compound according to claim 1, wherein the mesogen portion is an optionally substituted aromatic or aliphatic ring.

7. A chain polymeric liquid crystal compound according to claim 1, wherein the mesogen portion is selected from the group consisting of -continued

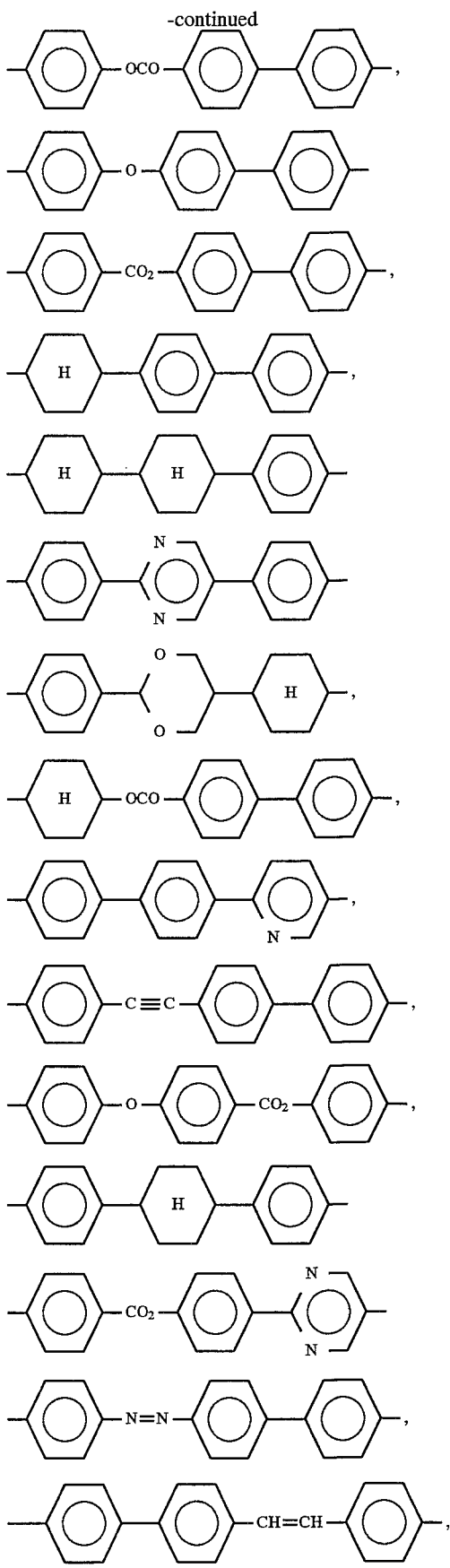

-continued

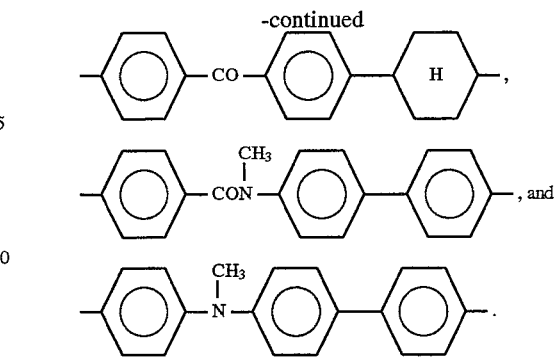

8. A chain polymeric liquid crystal compound according to claim 1, wherein X is —O—, —OCH$_2$—,

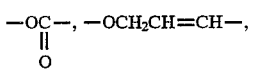

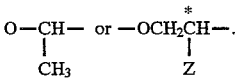

9. A polymeric liquid crystal composition comprising at least one of said chain polymeric liquid crystal compound according to claim 1, 2, or 8 and from 5–95 weight percent of at least one of a polymeric compound, a polymeric liquid crystal compound, a low molecular weight compound and a low molecular weight liquid crystal compound.

10. A polymeric liquid crystal composition according to claim 9, comprising said low molecular weight liquid crystal.

11. A polymeric liquid crystal device compromising at least one polymeric liquid crystal composition according to claim 9.

12. A display method, comprising selecting a chain polymeric liquid crystal compound or a polymeric liquid crystal composition according to claims 1, 2, or 8.

13. A method according to claim 12, further comprising the step of performing recording/reproducing.

14. A recording/reproducing device comprising:
a recording layer, said recording layer comprising a polymeric liquid crystal compound according to claims 1, 2 or 8.

15. A device according to claim 14, wherein said recording layer comprises a coloring material which absorbs and converts irradiated laser light into heat for performing recording.

16. A chain polymeric liquid crystal copolymer compound comprising a mesogen portion and a structure expressed by the following general formula (I) as a flexible spacer:

$$\mathrm{+X-Y-\underset{*}{\overset{\overset{\displaystyle F}{|}}{C}H}-CH_2-O\mathrm{\mathord{-}}\!\!\!\!\mathord{\mathrm{\mathord{\,\,}}}}\qquad \text{General Formula (I)}$$

(wherein X is —O—, —O—CH$_2$—CH$_2$—, —O—CH$_2$—,

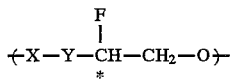

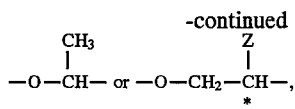

Y is —(CH$_2$)$_n$—(n=1 to 18), Z is a halogen atom, an alkyl group or an alkoxy group, and * is an asymmetric carbon atom).

17. A chain polymeric liquid crystal polyester compound comprising a structure according to claim 16 and expressed by general formula [I] as a flexible spacer.

18. A polymeric liquid crystal composition comprising at least one of said chain polymeric liquid crystal compound according to claim 16 or 17 and from 5–95 weight percent of at least one of a polymeric compound, a polymeric liquid crystal compound, a low molecular weight compound and a low molecular weight liquid crystal compound.

19. A polymeric liquid crystal composition according to claim 18 and containing low molecular weight liquid crystal.

20. A polymeric liquid crystal device containing at least one chain polymeric liquid crystal compound according to claim 16 or 17.

21. A polymeric liquid crystal device using at least one polymeric liquid crystal composition according to claim 19.

22. A display device, comprising a polymeric liquid crystal device according to claim 20.

23. A display device, comprising a polymeric liquid crystal device according to claim 21.

24. A recording/reproducing device, comprising an device according to claim 22.

25. A method of using a chain polymeric liquid crystal compound or a polymeric liquid crystal composition according to claim 16 or 17.

26. A method according to claim 25, further comprising the step of performing displaying.

27. A method according to claim 25, further comprising the step of performing recording/reproducing.

28. A chain polymeric liquid crystal copolymer according to claim 16, which has a numerical average molecular weight in the range of 2,000 to 1,000,000.

29. A chain polymeric liquid crystal copolymer according to claim 16, wherein the mesogen portion is an optionally substituted aromatic or aliphatic ring.

30. A chain polymeric liquid crystal copolymer according to claim 16, wherein the mesogen portion is selected from the group consisting of

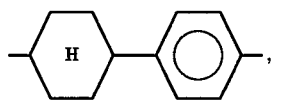

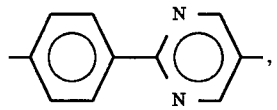

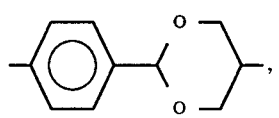

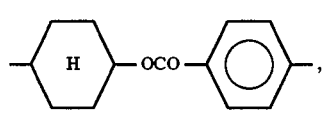

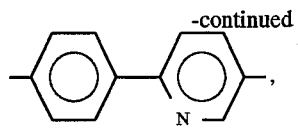

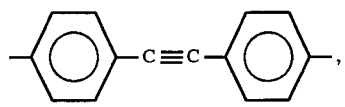

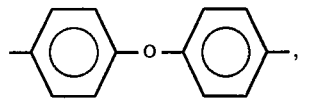

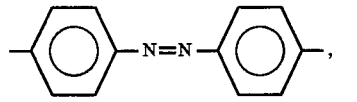

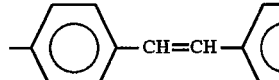

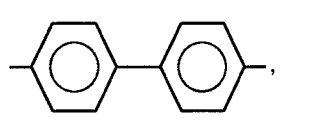

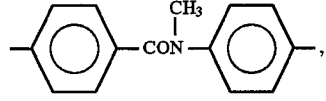

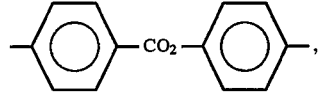

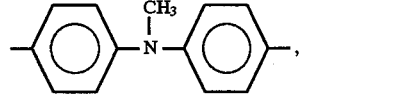

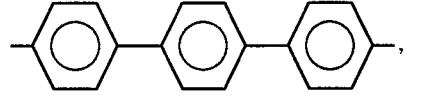

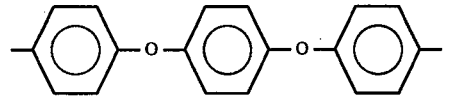

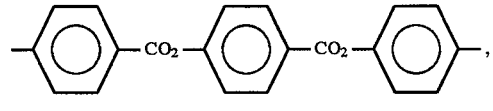

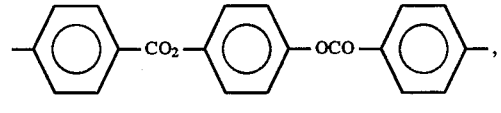

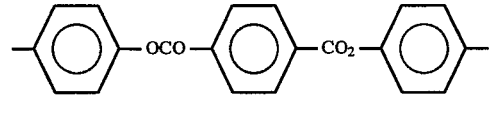

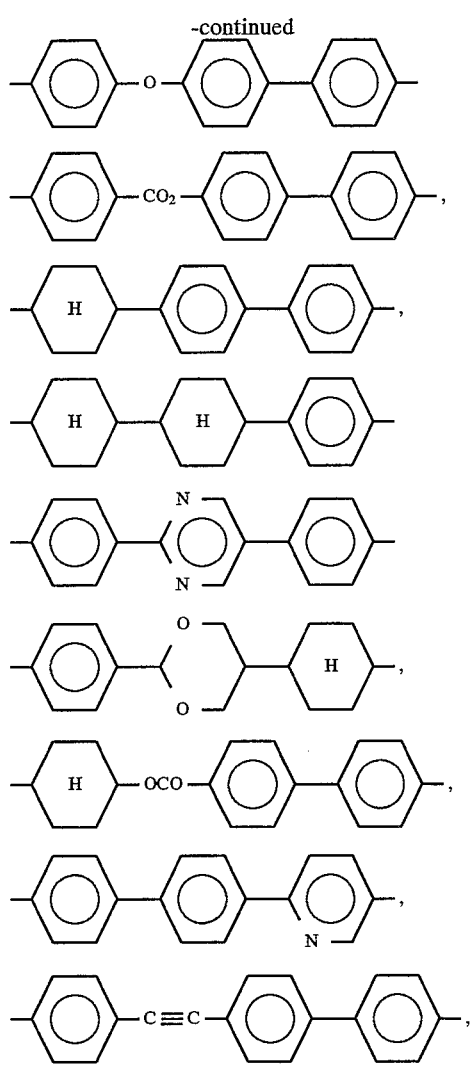
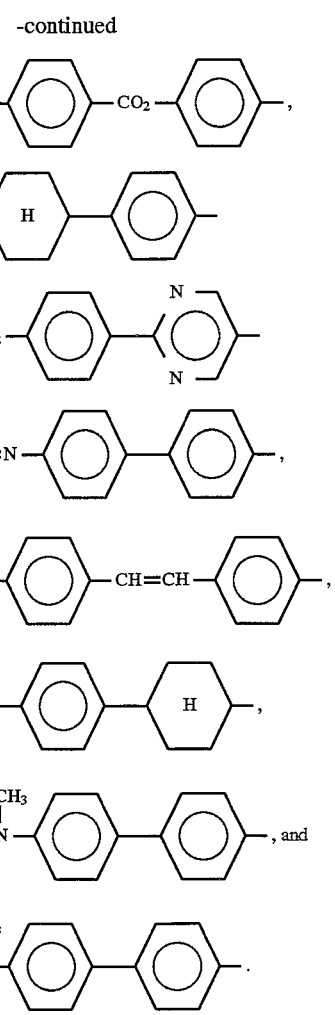

UNITED STATES PATENT AND TRADEMARK OFFICE
CERTIFICATE OF CORRECTION

PATENT NO. : 5,637,253

DATED : June 10, 1997

INVENTOR(S) : KOICHI SATO ET AL.

It is certified that error appears in the above-identified patent and that said Letters Patent is hereby corrected as shown below:

ON THE TITLE PAGE:

[57] ABSTRACT

Line 5, "and" should read --preferably with--.
Line 8, "and a low molecular weight liquid crystal compound" should be deleted.
Formula I, "—O—C should read ---O—C,
             ‖                      ‖
             O"                     O--.

COLUMN 2

Line 30, "polymer" should read --Polymer--.

COLUMN 3

Line 11, "—O—C should read ---O—C,
          ‖                     ‖
          O"                    O--.

COLUMN 4

Line 45, "—O—C should read ---O—C,
          ‖                     ‖
          O"                    O--.

UNITED STATES PATENT AND TRADEMARK OFFICE
CERTIFICATE OF CORRECTION

PATENT NO. : 5,637,253

DATED : June 10, 1997

INVENTOR(S): KOICHI SATO ET AL.

It is certified that error appears in the above-identified patent and that said Letters Patent is hereby corrected as shown below:

COLUMN 26

Formula (12)

"     (12)

4-hexyloxyphenyl-4-(2"-methylbutyl) biphenyl-4'-carboxylate

"

should read (12)

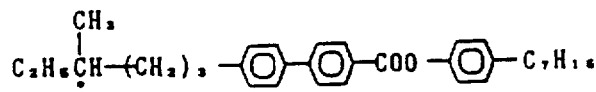

4-hexyloxyphenyl-4-(2"-methylbutyl) biphenyl-4'-carboxylate

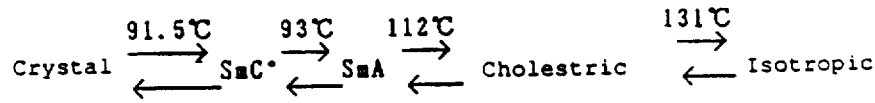

Line 55, "propyl)" should read --propyl--.

UNITED STATES PATENT AND TRADEMARK OFFICE
CERTIFICATE OF CORRECTION

PATENT NO. : 5,637,253

DATED : June 10, 1997

INVENTOR(S): KOICHI SATO ET AL.

It is certified that error appears in the above-identified patent and that said Letters Patent is hereby corrected as shown below:

COLUMN 43

Line 10, " 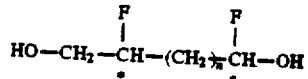 " should read -- 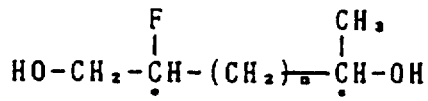 --.

Line 18, " 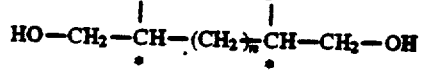 " should read -- 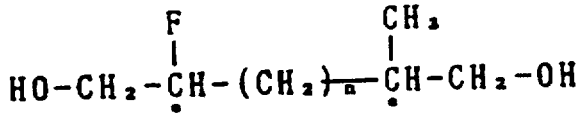 --.

COLUMN 53

Line 52, "propyl)" should read --propyl--.

COLUMN 56

Line 19, "an" should read --a--

COLUMN 62

Line 57, "polymer 6." should read --polymer e--.

UNITED STATES PATENT AND TRADEMARK OFFICE
CERTIFICATE OF CORRECTION

PATENT NO.  : 5,637,253

DATED       : June 10, 1997

INVENTOR(S) : KOICHI SATO ET AL.

It is certified that error appears in the above-identified patent and that said Letters Patent is hereby corrected as shown below:

COLUMN 69

Line 33, "atom)." should read --atom) with the proviso that when X=—OCH$_2$CH$_2$—, m must be 6 or more; when X=—OCH$_2$—, m must be 7 or more: and when X=—O—, m must be 8 or more.--.

COLUMN 72

Line 36, "compromising" should read --comprising--.

COLUMN 73

Line 29, "an" should read --a--.

Signed and Sealed this

Twentieth Day of January, 1998

Attest:

BRUCE LEHMAN

Attesting Officer

Commissioner of Patents and Trademarks